US008354250B2

(12) United States Patent
Okumoto et al.

(10) Patent No.: US 8,354,250 B2
(45) Date of Patent: Jan. 15, 2013

(54) NEUROTRANSMITTER SENSORS AND METHODS OF USING THE SAME

(75) Inventors: Sakiko Okumoto, Washington, DC (US); Loren L. Looger, Washington, DC (US); Wolf B. Frommer, Washington, DC (US)

(73) Assignee: Carnegie Institution of Washington, Washington, DC (US)

( * ) Notice: Subject to any disclaimer, the term of this patent is extended or adjusted under 35 U.S.C. 154(b) by 61 days.

(21) Appl. No.: 12/823,796

(22) Filed: Jun. 25, 2010

(65) Prior Publication Data

US 2011/0289609 A1 Nov. 24, 2011

Related U.S. Application Data

(62) Division of application No. 11/665,343, filed as application No. PCT/US2005/036956 on Oct. 14, 2005, now Pat. No. 7,777,016.

(60) Provisional application No. 60/643,576, filed on Jan. 14, 2005, provisional application No. 60/618,179, filed on Oct. 14, 2004.

(51) Int. Cl.
*C07K 19/00* (2006.01)
*C12N 15/62* (2006.01)
*G01N 33/567* (2006.01)

(52) U.S. Cl. ........ 435/69.7; 435/7.1; 436/501; 530/300; 536/23.4

(58) Field of Classification Search .................. None
See application file for complete search history.

(56) References Cited

U.S. PATENT DOCUMENTS

| 5,795,729 | A | 8/1998 | Lee |
| 5,981,200 | A | 11/1999 | Tsien |
| 6,197,534 | B1 | 3/2001 | Lakowicz |
| 6,376,257 | B1 | 4/2002 | Persechini |
| 6,465,199 | B1 | 10/2002 | Craig |
| 6,469,154 | B1 | 10/2002 | Tsien |
| 2002/0058273 | A1 | 5/2002 | Shipwash |
| 2003/0134346 | A1 | 7/2003 | Amiss |
| 2004/0029129 | A1 | 2/2004 | Wang |
| 2004/0118681 | A1 | 6/2004 | Hellinga |
| 2005/0112685 | A1 | 5/2005 | Amiss |
| 2005/0196768 | A1 | 9/2005 | Campbell |

FOREIGN PATENT DOCUMENTS

| WO | WO 00/49183 | 8/2000 |
| WO | WO 03/025220 | 3/2003 |

OTHER PUBLICATIONS

Nagai et al. "A variant of yellow fluorescent protein with fast and efficient maturation for cell-biological applications." Nature Biotechnology 20: 87-90, 2002.
De Lorimier et al. "Construction of a fluorescent biosensor family." Protein Science 11: 2655-2675, 2002.
Dwyer et al. "Periplasmic binding proteins: A versatile superfamily for protein engineering." Current Opinion in Structural Biology 14: 495-504, 2004.
Sigmund "Viewpoint: are studies in genetically altered mice out of control?" Arterioscler. Thromb. Vasc. Biol. 20: 1425-1429, 2000.
Miyawaki et al. "Fluorescent indicators for Ca2+ based on green fluorescent proteins and clamodulin." Nature 388: 882-887, 1997.
Mitra et al. "Fluorescence resonance energy transfer between blue-emitting and red-shifted excitation derivatives of the green fluorescent protein." Gene 173: 13-17, 1996.
Benson et al. "Design of bioelectronic interfaces by exploiting hinge-bending motions in proteins." Science 293: 1641-1644, 2001.
Fehr et al. "Visualization of maltose uptake in living yeast cells by fluorescent nanosensors." PNAS 99: 9846-9851, 2002.
Jenne et al. "Real-time characterization of ribozymes by fluorescence resonance energy transfer (FRET)." Angewandte Chemie 38: 1300-1303, 1999.
Schafer et al. "X-ray structures of the maltose-maltodextrin-binding protein of the thermophilic bacterium *Alicyclobacillus acidocaldarius* provide insight into acid stability of proteins." J. Mol. Biol. 335: 261-274, 2004.
Deuschle et al. "Construction and optimization of a family of genetically encoded metabolite sensors by semirational protein engineering." Protein Science 14: 2304-2314, 2005.
Widersten et al. "Optimized heterologous expression of the polymorphic human glutathione transferase M1-1 based on silent mutations in the corresponding cDNA." Protein Expression and Purification 7: 367-371, 1996.
Wood et al. PRI-80 Database, Accession No. AI2966, Jul. 9, 2004, The Genome of the Natural Genetic Engineer *Agrobacterium tumefaciens* C58, Yoo et al. Science 294: 2317-2323, 2001.
Tolosa et al. "Glucose sensor for low-cost lifetime-based sensing using a genetically engineered protein." Analytical Biochemistry 267: 114-120, 1999.
Zhang et al. "Genetically encoded reporters of protein kinase A activity reveal impact of substrate tethering." PNAS 98: 14997-15002, 2001.
De et al. "Novel biosensors for the detection of estrogen receptor ligands." Journal of Steroid Biochemistry and Molecular Biology 96: 235-244, 2005.
Xu et al. "Kinetic and thermodynamic studies of purine repressor binding to corepressor and operator DNA." Journal of Biological Chemistry 273: 8058-8064, 1998.
Gunsalus et al. "Nucleotide sequence and expression of *Escherichia coli trpR*, the structural gene for the *trp* aporepressor." PNAS 77: 7117-7121, 1980.
Gaits et al. "Shedding light on cell signaling: Interpretation of FRET biosensors." Science's STKE: signal transduction knowledge environment: 165 (PE3): 1-5, 2003.
Chen et al. "Protein localization in living cells and tissues using FRET and FLIM." Differentiation 71: 528-541, 2003.
Tsien "Building and breeding molecules to spy on cells and tumors." FEBS Lett. 579: 927-932, 2005.

*Primary Examiner* — John Ulm
(74) *Attorney, Agent, or Firm* — Morgan, Lewis & Bockius LLP

(57) ABSTRACT

Neurotransmitter biosensors are disclosed, including YbeJ-based glutamate binding biosensors, comprising a neurotransmitter binding domain conjugated to donor and fluorescent moieties that permit detection and measurement of Fluorescence Resonance Energy Transfer upon binding neurotransmitter. Such biosensors are useful for the detection of neurotransmitter concentrations in vivo and in culture.

28 Claims, 5 Drawing Sheets

NEUROTRANSMITTER SENSORS AND METHODS OF USING THE SAME

CROSS-REFERENCE TO RELATED APPLICATIONS

The present application is divisional of U.S. patent application Ser. No. 11/665,343, filed Apr. 13, 2007, now U.S. Pat. No. 7,777,016 which is a U.S. National Phase Application of International Application No. PCT/US2005/036956, filed Oct. 14, 2005, which claims the benefit of U.S. Provisional Patent Application 60/618,179, filed Oct. 14, 2004, and U.S. Provisional Patent Application 60/643,576, filed Jan. 14, 2005, which are incorporated herein by reference in their entireties.

This application is also related to provisional application Ser. No. 60/658,141, provisional application Ser. No. 60/658,142, provisional application Ser. No. 60/657,702, PCT application No. PCT/US2005/036955, PCT application No. PCT/US2005/036953, and PCT application no. PCT/US2005/036951, which are herein incorporated by reference in their entireties.

STATEMENT REGARDING FEDERALLY SPONSORED RESEARCH OR DEVELOPMENT

This invention was funded through two grants, including an NIH subcontract from Duke University (Subcontract No. SPSID 126632) and a Human Frontier Science Program grant (Contract No. RGP0041/2004C). This invention was also funded by DOE Grant No. DE-FG02-04ER15542 and by NIH Grant No. 1 R33DK070272. Accordingly the U.S. Government has certain rights to this invention.

FIELD OF INVENTION

The invention relates generally to the field of neurotransmitter signaling and, more specifically, to biosensors and methods for measuring and detecting changes in neurotransmitter levels using fluorescence resonance energy transfer (FRET).

BACKGROUND OF INVENTION

All publications and patent applications herein are incorporated by reference to the same extent as if each individual publication or patent application was specifically and individually indicated to be incorporated by reference.

The publications discussed herein are provided solely for their disclosure prior to the filing date of the present application. Nothing herein is to be construed as an admission that the present invention is not entitled to antedate such publication by virtue of prior invention.

Glutamate is an amino acid and one type of neurotransmitter found in the brain. Glutamatergic neurons are the predominant excitatory pathways in the mammalian brain, representing one-third of all rapid excitatory synapses in the central nerve system (Cotman, C. W., and Monaghan, D. T. (1986) Anatomical organization of excitatory amino acid receptors and their properties. Adv. Exp. Med. Biol. 203, 237-252). Signaling by glutamate is mediated by a large and diverse number of receptors, including ionotropic receptors that allow passage of extracellular calcium through coupled ion channels upon activation, and metabotropic receptors that activate intermediary molecules such as G proteins to produce molecules such as $IP_3$ that increase cytosolic calcium concentrations. Interaction between neurons may be either excitatory or inhibitory. The major excitatory amino acid neurotransmitters are glutamate and aspartate, while GABA (γ-aminobutyric acid), glycine (aminoacetic acid), and taurine are inhibitory (Mark et al. (2001) American Journal of Neuroradiology 22:1813-1824).

Clearance of extracellular glutamate by glutamate transporters is an indispensable step to prevent the accumulation of glutamate, which would otherwise result in overstimulation of glutamate receptors and glutamate excitotoxicity. Excitotoxic damage causes, or is involved in, a number of neurologic diseases, including stroke, trauma, epilepsy, and neurodegenerative conditions, such as Huntington disease, AIDS dementia complex, and amyotrophic lateral sclerosis (Doble, A., Louvel, E., and Hugon, J. (1999) The role of excitotoxicity in neurodegenerative disease: implications for therapy, Pharmacol. Ther. 81(3):163-221; Waggie K S, Kahle P J, Tolwani R J. (1999) Neurons and mechanisms of neuronal death in neurodegenerative diseases: a brief review. Lab. Anim. Sci. 49:358-362). Glutamate receptor overstimulation increases intracellular calcium by directly opening ion channels, allowing the influx of calcium and causing membrane depolarization. Depolarization in turn activates voltage-dependent calcium channels, which further increases the intracellular calcium levels. The glutamate-induced elevated calcium levels causes overactivation of a number of enzymes, including protein kinase C, calcium/calmodulin-dependent protein kinase II, phospholipases, proteases, phosphatases, nitric oxide synthase, endonucleases, and ornithine decarboxylase, some of which produce toxic free oxygen radicals, or produce positive feedback loops leading to neuronal death (Mark et al., 2001).

The key factor that triggers the excitotoxic cascade is the excessive accumulation of glutamate in the synaptic space. Normal extracellular glutamate concentration is about 0.6 μmol/L, with substantial neuronal excitotoxic injury occurring at glutamate concentrations of 2 to 5 μmol/L. Traumatic injury to neurons can produce disastrous results with the release of about 10 μmol/L to the extracellular space. Given the ensuing cascade, injury to a single neuron puts all of the neighboring neurons at risk (Mark et al., 2001).

Despite a number of studies showing the involvement of higher glutamate concentration in neurologic diseases, measuring glutamate concentration in living cells remains challenging. One of the most important tools required to assign functions of neurons in vivo would be to visualize glutamate fluxes directly. The extracellular concentration of glutamate has been measured by in vivo microdialysis techniques (Faden, A. I., Demediuk, P., Panter, S. S., and Vink, R. (1989) The role of excitatory amino acids and NMDA receptors in traumatic brain injury. Science 244, 798-800; Fallgren, A. B., and Paulsen, R. E. (1996) A microdialysis study in rat brain of dihydrokainate, a glutamate uptake inhibitor. Neurochem Res 21, 19-25). However, microdialysis is limited in spatial and temporal resolution, unable to detect the localized and rapid concentration change around a single synapse. In addition, the in vivo microdialysis technique is destructive. It also does not permit direct monitoring of glutamate levels inside living neurons or astrocytes.

In vivo measurement of ions and metabolites by using Fluorescence Resonance Energy Transfer (FRET) has been successfully used to measure calcium concentration changes, by fusing CFP, YFP, and a reporter domain consisting of calmodulin and the M13 peptide (Zhang, J., Campbell, R. E., Ting, A. Y., and Tsien, R. Y. (2002a) Creating new fluorescent probes for cell biology. Nat Rev Mol Cell Biol 3, 906-918; Zhang, J., Campbell, R. E., Ting, A. Y., and Tsien, R. Y. (2002b) Creating new fluorescent probes for cell biology.

Nature Reviews Molecular Cell Biology 3, 906-918). Binding of calcium to calmodulin causes global structural rearrangement of the chimera resulting in a change in FRET intensity as mediated by the donor and acceptor fluorescent moieties. Recently a number of bacterial periplasmic binding proteins, which undergo a venus flytrap-like closure of two lobes upon substrate binding, have been successfully used as the scaffold of metabolite nanosensors (Fehr, M., Frommer, W. B., and Lalonde, S. (2002) Visualization of maltose uptake in living yeast cells by fluorescent nanosensors. Proc. Natl. Acad. Sci. USA 99, 9846-9851; Fehr, M., Lalonde, S., Lager, I., Wolff, M. W., and Frommer, W. B. (2003) In vivo imaging of the dynamics of glucose uptake in the cytosol of COS-7 cells by fluorescent nanosensors. J. Biol. Chem. 278, 19127-19133; Lager, I., Fehr, M., Frommer, W. B., and Lalonde, S. (2003) Development of a fluorescent nanosensor for ribose. FEBS Lett 553, 85-89).

In order to develop a nanosensor protein for glutamate, we searched for a protein which changes conformation upon binding glutamate. The family of ionotropic (iGluRs) and metabotropic glutamate receptor (mGluRs) have an extracellular ligand binding domain which has sequence similarity to bacterial periplasmic binding proteins (O'Hara, P. J., Sheppard, P. O., Thogersen, H., Venezia, D., Haldeman, B. A., McGrane, V., Houamed, K. M., Thomsen, C., Gilbert, T. L., and Mulvihill, E. R. (1993) The ligand-binding domain in metabotropic glutamate receptors is related to bacterial periplasmic binding proteins. Neuron 11, 41-52), as well as the ligand binding domain of γ-aminobytyric acid $(GABA)_B$ receptor (Kaupmann, K., Huggel, K., Heid, J., Flor, P. J., Bischoff, S., Mickel, S. J., McMaster, G., Angst, C., Bittiger, H., Froestl, W., and Bettler, B. (1997) Expression cloning of GABA(B) receptors uncovers similarity to metabotropic glutamate receptors. Nature 386, 239-246). The crystal structures of mGluR1 ligand binding domain in three different forms, in a complex with glutamate and in two unliganded forms, has been determined (Kunishima, N., Shimada, Y., Tsuji, Y., Sato, T., Yamamoto, M., Kumasaka, T., Nakanishi, S., Jingami, H., and Morikawa, K. (2000). Structural basis of glutamate recognition by a dimeric metabotropic glutamate receptor. Nature 407, 971-977), and the results suggested that glutamate binding stabilizes the closed conformation. Galvez et al. suggested that the ligand binding domain of $GABA_B$ receptor also undergoes the closure of two lobes (Galvez, T., Parmentier, M. L., Joly, C., Malitschek, B., Kaupmann, K., Kuhn, R., Bittiger, H., Froestl, W., Bettler, B., and Pin, J. P. (1999). Mutagenesis and modeling of the GABAB receptor extracellular domain support a venus flytrap mechanism for ligand binding. J Biol Chem 274, 13362-13369). We therefore attempted to construct FRET biosensors using the mGluR and $GABA_B$ receptors and assayed for changes in FRET efficiency upon addition of substrates. However, no change in FRET efficiency was observed. Similarly, also the LIV leucine/isoleucine/valine amino acid binding protein from bacteria could not be engineered into a functional FRET sensor.

De Lorimier et al. have shown that the YbeJ protein from *E. coli*, which shares sequence homology to glutamine- and histidine-binding proteins, and which is located in an operon involved in glutamate metabolism, binds to glutamate and aspartate (de Lorimier, R. M., Smith, J. J., Dwyer, M. A., Looger, L. L., Sali, K. M., Paavola, C. D., Rizk, S. S., Sadigov, S., Conrad, D. W., Loew, L., and Helling a, H. W. (2002) Construction of a fluorescent biosensor family. Protein Sci 11, 2655-2675). The similarity of YbeJ to glutamine and histidine binding proteins from bacteria lead us to generate homology models based on the solved crystal structures of these two proteins. The 3D structure of the glutamine and histidine binding proteins indicates that N- and C-termini of these proteins are located on the same lobe, therefore the closure of two lobes upon substrate binding is unlikely to change the distance between N- and C-terminus. Thus none of these proteins should permit the construction of a FRET sensor on the same principle. Indeed, the sensors proposed by Helling a and Looger in published U.S. patent application 20040118681 propose conjugating a single fluorophore to a cysteine residue that responds to a conformational change upon ligand binding, in contrast to the dual fluorescent moieties used for FRET.

Nevertheless, the present inventors have surprisingly found that the YbeJ protein of *E. coli* is an efficient FRET scaffold for detecting glutamate binding, despite the finding that both termini are located on the same lobe of the protein. This is in contrast to the general hypothesis that distance changes are converted to FRET changes.

SUMMARY OF INVENTION

The present invention provides neurotransmitter biosensors for detecting and measuring changes in neurotransmitter concentrations. In particular, the invention provides an isolated nucleic acid encoding a glutamate binding fluorescent indicator (FLIP-E) comprising a glutamate binding protein moiety from *Escherichia coli* YbeJ wherein the glutamate binding protein moiety is genetically fused to a donor fluorescent protein moiety and an acceptor fluorescent protein moiety, wherein fluorescence resonance energy transfer (FRET) between the donor moiety and the acceptor moiety is altered when the donor moiety is excited and glutamate binds to the glutamate binding protein moiety. Vectors, including expression vectors, and host cells comprising the inventive nucleic acids are also provided, as well as biosensor proteins encoded by the nucleic acids. Such nucleic acids, vectors, host cells and proteins may be used in methods of detecting changes in neurotransmitter levels and particularly extracellular glutamate levels in neuron samples, and in methods of identifying compounds that modulate glutamate excitotoxicity.

DETAILED DESCRIPTION OF INVENTION

Figure 1:
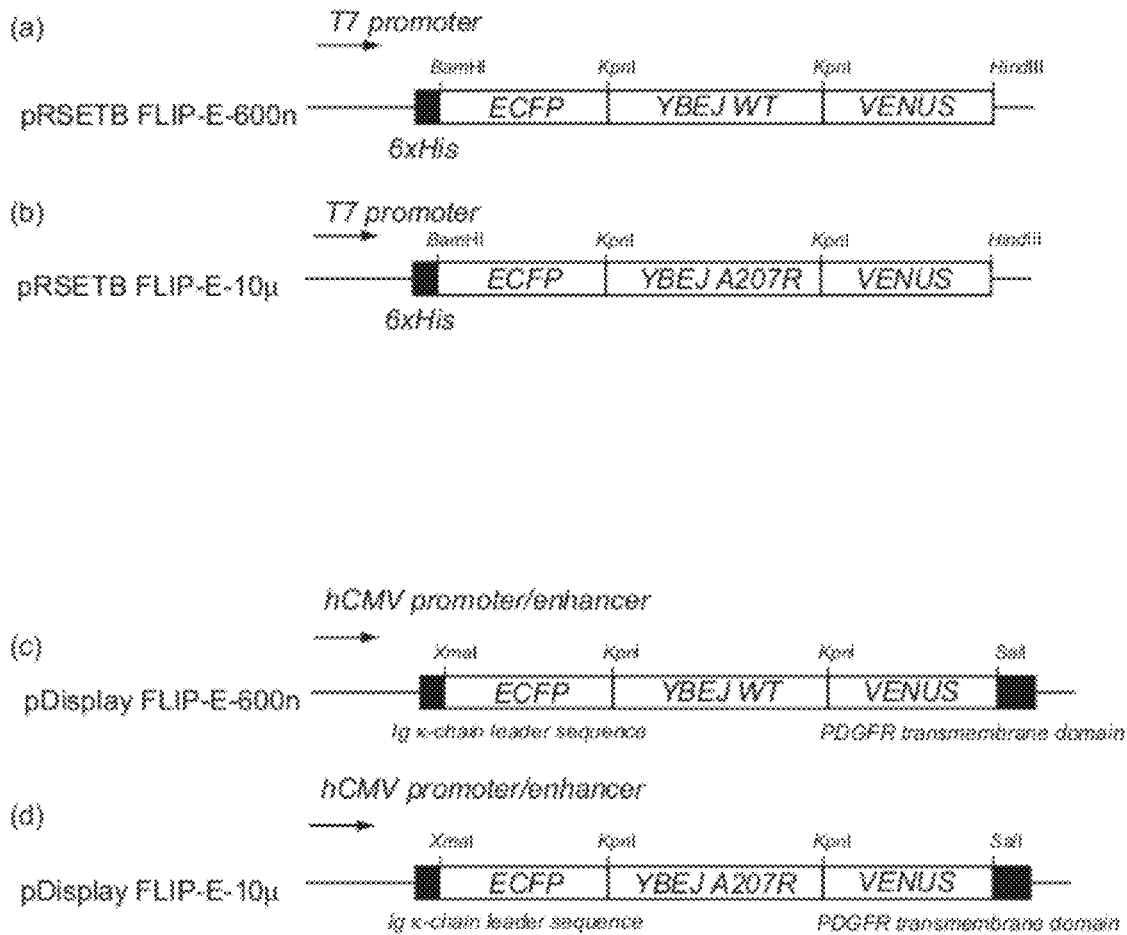
FIG. 1. FLIP-E nanosensor constructs used for expression in *E. coli* (A and B) and neuronal cell culture (C and D).

The following description includes information that may be useful in understanding the present invention. It is not an admission that any of the information provided herein is prior art or relevant to the presently claimed inventions, or that any publication specifically or implicitly referenced is prior art.

Other objects, advantages and features of the present invention become apparent to one skilled in the art upon reviewing the specification and the drawings provided herein. Thus, further objects and advantages of the present invention will be clear from the description that follows.

Biosensors

The present invention provides neurotransmitter biosensors for detecting and measuring changes in neurotransmitter concentrations using Fluorescence Resonance Energy Transfer (FRET). The three major categories of substances that act as neurotransmitters are (1) amino acids (primarily glutamic acid or glutamate, GABA, aspartic acid & glycine), (2) peptides (vasopressin, somatostatin, neurotensin, etc.) and (3) monoamines (norepinephrine, dopamine & serotonin) plus acetylcholine. In particular, the invention provides glutamate binding fluorescent indicators, particularly indicators comprising a glutamate binding protein moiety from the *Escherichia coli* glutamate/aspartate receptor, YbeJ. Additional neurotransmitter biosensors for the neurotransmitters listed above may also be prepared using the constructs and methods provided herein.

Thus, the invention provides isolated nucleic acids encoding neurotransmitter binding fluorescent indicators. One embodiment, among others, is an isolated nucleic acid which encodes a glutamate binding fluorescent indicator, the indicator comprising: a glutamate binding protein moiety, a donor fluorescent protein moiety genetically fused to the glutamate binding protein moiety, and an acceptor fluorescent protein moiety genetically fused to the glutamate binding protein moiety, wherein FRET between the donor moiety and the acceptor moiety is altered when the donor moiety is excited and glutamate binds to the glutamate binding protein moiety. A preferred glutamate binding protein moiety is a glutamate binding protein moiety from *Escherichia coli* YbeJ.

YbeJ is also known in the art as YzzK and Gltl, and its DNA sequence (SEQ ID NO: 1) and protein sequence (YbeJ, protein accession no NP_415188, SEQ ID NO: 2) are known. Any portion of the YbeJ DNA sequence which encodes a glutamate binding region may be used in the nucleic acids of the present invention. For instance, one region that is suitable for use in the nucleic acids of the present invention is provided by SEQ ID NO: 3, which encodes a truncated glutamate-aspartate binding protein sequence SEQ ID NO: 4), encoding mature protein without signal peptide. Naturally occurring homologues from other bacterial species may also be used, for instance the PA5082 gene from *Pseudomonas aeruginosa*, whose gene product is 70% similar to the YbeJ protein from *E. coli*. Glutamate binding portions of YbeJ or any of its homologues may be cloned into the vectors described herein and screened for activity according to the disclosed assays.

Naturally occurring species variants of YbeJ may also be used, in addition to artificially engineered variants comprising site-specific mutations, deletions or insertions that maintain measurable glutamate binding function. Variant nucleic acid sequences suitable for use in the nucleic acid constructs of the present invention will preferably have at least 70, 75, 80, 85, 90, 95, or 99% similarity or identity to the gene sequence for YbeJ. Suitable variant nucleic acid sequences may also hybridize to the gene for YbeJ under highly stringent hybridization conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

Preferred artificial variants of the present invention may exhibit increased or decreased affinity for glutamate, in order to expand the range of concentration that can be measured by YbeJ-based and other glutamate nanosensors. Preferred artificial variants, among others, include glutamate binding regions comprising the mutations A207G, A207P, A207K A207M, A207S, A207C, A207R, A207V, A207L, A207Q, A207T, A207F, A207Y, A207N, A207W, A207H, A207D, and/or S95W. Additional artificial variants showing decreased or increased binding affinity for glutamate may be constructed by random or site-directed mutagenesis and other known mutagenesis techniques, and cloned into the vectors described herein and screened for activity according to the disclosed assays.

The isolated nucleic acids of the invention may incorporate any suitable donor and acceptor fluorescent protein moieties that are capable in combination of serving as donor and acceptor moieties in FRET. Preferred donor and acceptor moieties are selected from the group consisting of GFP (green fluorescent protein), CFP (cyan fluorescent protein), BFP (blue fluorescent protein), YFP (yellow fluorescent protein), and enhanced variants thereof, with a particularly preferred embodiment provided by the donor/acceptor pair CFP/YFP-Venus, a variant of YFP with improved pH tolerance and maturation time (Nagai, T., Ibata, K., Park, E. S., Kubota, M., Mikoshiba, K., and Miyawaki, A. (2002) A variant of yellow fluorescent protein with fast and efficient maturation for cell-biological applications. Nat. Biotechnol. 20, 87-90). An alternative is the MiCy/mKO pair with higher pH stability and a larger spectral separation (Karasawa S, Araki T, Nagai T, Mizuno H, Miyawaki A. Cyan-emitting and orange-emitting fluorescent proteins as a donor/acceptor pair for fluorescence resonance energy transfer. Biochem J. 2004 381:307-12). Criteria to consider when selecting donor and acceptor fluorescent moieties are known in the art, for instance as disclosed in U.S. Pat. No. 6,197,928, which is herein incorporated by reference in its entirety.

Also suitable as either a donor or acceptor is native DsRed from a Discosoma species, an ortholog of DsRed from another genus, or a variant of a native DsRed with optimized properties (e.g. a K83M variant or DsRed2 (available from Clontech)). As used herein, the term "variant" is intended to refer to polypeptides with at least about 70%, more preferably at least 75% identity, including at least 80%, 90%, 95% or greater identity to native fluorescent molecules. Many such variants are known in the art, or can be readily prepared by random or directed mutagenesis of native fluorescent molecules (see, for example, Fradkov et al., FEBS Lett. 479:127-130 (2000)).

When the fluorophores of the biosensor contain stretches of similar or related sequence(s), the present inventors have recently discovered that gene silencing may adversely affect expression of the biosensor in certain cells and particularly whole organisms. In such instances, it is possible to modify the fluorophore coding sequences at one or more degenerate or wobble positions of the codons of each fluorophore, such that the nucleic acid sequences of the fluorophores are modified but not the encoded amino acid sequences. Alternative, one or more conservative substitutions that do not adversely affect the function of the fluorophores may also be incorporated. See PCT application No. PCT/US2005/036953, which is herein incorporated by reference in its entirety.

The invention further provides vectors containing isolated nucleic acid molecules encoding neurotransmitter biosensor polypeptides. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. Such vectors include expression vectors containing expression control sequences operatively linked to the nucleic acid sequence coding for the neurotransmitter biosensor. Vectors may be adapted for function in a prokaryotic cell, such as $E.\ coli$ or other bacteria, or a eukaryotic cell, including yeast and animal cells. For instance, the vectors of the invention will generally contain elements such as an origin of replication compatible with the intended host cells, one or more selectable markers compatible with the intended host cells and one or more multiple cloning sites. The choice of particular elements to include in a vector will depend on factors such as the intended host cells, the insert size, whether regulated expression of the inserted sequence is desired, i.e., for instance through the use of an inducible or regulatable promoter, the desired copy number of the vector, the desired selection system, and the like. The factors involved in ensuring compatibility between a host cell and a vector for different applications are well known in the art.

Preferred vectors for use in the present invention will permit cloning of the neurotransmitter binding domain or receptor between nucleic acids encoding donor and acceptor fluorescent molecules, resulting in expression of a chimeric or fusion protein comprising the neurotransmitter binding domain genetically fused to donor and acceptor fluorescent molecules. Exemplary vectors include the bacterial pRSET-FLIP derivatives disclosed in Fehr et al. (2002) (Visualization of maltose uptake in living yeast cells by fluorescent nanosensors. Proc. Natl. Acad. Sci. USA 99, 9846-9851), which is herein incorporated by reference in its entirety. Alternatively, the neurotransmitter binding domain of interest may be first fused to fluorescent donor and acceptor coding sequences and then cloned into an appropriate vector, as described in U.S. Pat. No. 6,596,499, which is herein incorporated by reference in its entirety.

The chimeric nucleic acids of the present invention are preferably constructed such that the donor and acceptor fluorescent moiety coding sequences are fused to separate termini of the neurotransmitter binding domain in a manner such that changes in FRET between donor and acceptor may be detected upon neurotransmitter binding. Alternatively, either or both of the donor fluorophore and/or said acceptor fluorophore moieties may be fused to the ligand binding protein moiety at an internal site of said ligand binding protein moiety. Such fusions are described in provisional application No. 60/658,141, which is herein incorporated by reference. Preferably, the donor and acceptor moieties are not fused in tandem, although the donor and acceptor moieties may be contained on the same protein domain or lobe. A domain is a portion of a protein that performs a particular function and is typically at least about 40 to about 50 amino acids in length. There may be several protein domains contained in a single protein.

Fluorescent domains can optionally be separated from the neurotransmitter binding domain by one or more flexible linker sequences. Such linker moieties are preferably between about 1 and 50 amino acid residues in length, and more preferably between about 1 and 30 amino acid residues. Linker moieties and their applications are well known in the art and described, for example, in U.S. Pat. Nos. 5,998,204 and 5,981,200, and Newton et al., Biochemistry 35:545-553 (1996). Alternatively, shortened versions of the fluorophores or the binding protein may be used.

For instance, the present inventors have also found that removing sequences connecting the core protein structure of the binding domain and the fluorophore, i.e., by removing linker sequences and/or by deleting amino acids from the ends of the analyte binding moiety and/or the fluorophores, closer coupling of fluorophores is achieved leading to higher ratio changes. Preferably, deletions are made by deleting at least one, or at least two, or at least three, or at least four, or at least five, or at least eight, or at least ten, or at least fifteen nucleotides in a nucleic acid construct encoding a FRET biosensor that are located in the regions encoding the linker, or fluorophore, or ligand binding domains. Deletions in different regions may be combined in a single construct to create more than one region demonstrating increased rigidity. Amino acids may also be added or mutated to increase rigidity of the biosensor and improve sensitivity. For instance, by introducing a kink by adding a proline residue or other suitable amino acid. Improved sensitivity may be measured by the ratio change in FRET fluorescence upon ligand binding, and preferably increases by at least a factor of 2 as a result of said deletion(s). See provisional application No. 60/658,141, which is herein incorporated by reference in its entirety.

The invention also includes host cells transfected with a vector or an expression vector of the invention, including prokaryotic cells, such as $E.\ coli$ or other bacteria, or eukaryotic cells, such as yeast cells or animal cells. In another aspect, the invention features a transgenic non-human animal having a phenotype characterized by expression of the nucleic acid sequence coding for the expression of the neurotransmitter biosensor. The phenotype is conferred by a transgene contained in the somatic and germ cells of the animal, which may be produced by (a) introducing a transgene into a zygote of an animal, the transgene comprising a DNA construct encoding the neurotransmitter biosensor; (b) transplanting the zygote into a pseudopregnant animal; (c) allowing the zygote to develop to term; and (d) identifying at least one transgenic offspring containing the transgene. The step of introducing of the transgene into the embryo can be by introducing an embryonic stem cell containing the transgene into the embryo, or infecting the embryo with a retrovirus containing the transgene. Preferred transgenic animals will express the encoded neurotransmitter biosensor in the brain. Transgenic animals of the invention include transgenic *C. elegans* and transgenic mice and other animals.

The present invention also encompasses isolated neurotransmitter biosensor molecules having the properties described herein, particularly YbeJ-based glutamate binding fluorescent indicators. Such polypeptides may be recombinantly expressed using the nucleic acid constructs described herein, or produced by chemically coupling some or all of the component domains. The expressed polypeptides can optionally be produced in and/or isolated from a transcription-translation system or from a recombinant cell, by biochemical and/or immunological purification methods known in the art. The polypeptides of the invention can be introduced into a lipid bilayer, such as a cellular membrane extract, or an artificial lipid bilayer (e.g. a liposome vesicle) or nanoparticle.

Methods of Detecting Levels of Neurotransmitters

The nucleic acids and proteins of the present invention are useful for detecting and measuring changes in the levels of neurotransmitters in the brain or nervous system of an animal, particularly changes in the level of extracellular glutamate, which can be a signal of a disorder or disease associated with glutamate excitotoxicity. In one embodiment, the invention comprises a method of detecting changes in the level of extracellular glutamate in a sample of neurons, comprising (a) providing a cell expressing a nucleic acid encoding a glutamate binding biosensor as described herein and a sample of neurons; and (b) detecting a change in FRET between a donor fluorescent protein moiety and an acceptor fluorescent protein moiety, each covalently attached to the glutamate binding domain, wherein a change in FRET between said donor moiety and said acceptor moiety indicates a change in the level of extracellular glutamate in the sample of neurons. Alternatively, the protein may be produced in a heterologous host, e.g. in bacteria, purified and injected into organs directly or into the intercellular spaces. The protein or derivatives thereof may also be coupled to particles including quantum dots and introduced into cells or compartments.

FRET may be measured using a variety of techniques known in the art. For instance, the step of determining FRET may comprise measuring light emitted from the acceptor fluorescent protein moiety. Alternatively, the step of determining FRET may comprise measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety. The step of determining FRET may also comprise measuring the excited state lifetime of the donor moiety or anisotropy changes (Squire A, Verveer P J, Rocks O, Bastiaens P I. J Struct Biol. 2004 July; 147(1):62-9. Red-edge anisotropy microscopy enables dynamic imaging of homo-FRET between green fluorescent proteins in cells.). Such methods are known in the art and described generally in U.S. Pat. No. 6,197,928, which is herein incorporated by reference in its entirety.

The amount of glutamate or other neurotransmitter in a sample of neurons can be determined by determining the degree of FRET. First the FLIP-E sensor must be introduced into the sample. Changes in neurotransmitter concentration can be determined by monitoring FRET changes at time intervals. The amount of neurotransmitter in the sample can be quantified for example by using a calibration curve established by titration in vivo.

The neuron sample to be analyzed by the methods of the invention may be contained in vivo, for instance in the measurement of glutamate efflux on the surface of hippocampal neurons, or in vitro, wherein glutamate efflux is measured in neuronal cell culture. Alternatively, a fluid extract from the brain or one or more synaptic spaces may be used as a sample from which extracellular neurotransmitter is detected or measured. Such measurements may be used to detect extracellular glutamate associated with traumatic injury to said neurons, or as a possible indicator of a neurological disorder associated with glutamate excitotoxicity, including stroke, epilepsy, Huntington disease, AIDS dementia complex, and amyotrophic lateral sclerosis, among others.

Methods for detecting neurotransmitter levels as disclosed herein may be used to screen and identify compounds that may be used to modulate neurotransmitter concentrations and particularly compounds useful for modulating glutamate excitotoxicity. In one embodiment, among others, the invention comprises a method of identifying a compound that modulates glutamate excitotoxicity comprising (a) contacting a cell expressing a glutamate biosensor as disclosed herein and a sample of neurons with one or more test compounds, and (b) determining FRET between said donor fluorescent domain and said acceptor fluorescent domain following said contacting, wherein increased or decreased FRET following said contacting indicates that said test compound is a compound that modulates glutamate excitotoxicity. The term "modulate" means that such compounds may increase or decrease glutamate excitotoxicity. Compounds that increase glutamate levels are targets for therapeutic intervention and treatment of disorders associated with glutamate excitotoxicity, as described above. Compounds that decrease glutamate levels may be developed into therapeutic products for the treatment of disorders associated with glutamate excitotoxicity.

The targeting of the sensor to the outer leaflet of the plasma membrane is only one embodiment of the potential applications. It demonstrates that the nanosensor can be targeted to a specific compartment. Alternatively, other targeting sequences may be used to express the sensors in other compartments such as vesicles, ER, vacuole, etc.

Expression systems comprise not only rat neurons, but also human cell lines, animal cells and organs, fungi and plant cells. The sensors can also be used to monitor levels of glutamate in fungal and plant organisms where glutamate serves as an important nitrogen compound, but potentially also a signaling molecule. Expression in bacteria may be used to monitor glutamate levels at sites of infection or in compartments in which the bacteria reside or are introduced.

Specifically, bacteria or fungi expressing the sensors may serve as biosensors or as tools to identify new pesticides using a similar scheme as outlined for drug screening above.

Additional Utilities

The biosensors of the present invention can also be expressed on the surface of animal cells to determine the function of neurons. For example, in *C. elegans*, many of the neurons present have not been assigned a specific function. Expression of the biosensors on the surface permits visualization of neuron activity in living worms in response to stimuli, permitting assignment of function and analysis of neuronal networks. Similarly, the introduction of multiphoton probes into the brain of living mice or rats, permits imaging these processes. Finally, expression in specific neurons or glia will allow the study of phenomena such as stroke or Alzheimers Disease and the effect of such disorders on glutamate levels inside neuronal cells or on their surface. Moreover, the effect of medication on localized brain areas or neuronal networks can be studied in vivo.

Finally, it is possible to use the sensors as tools to modify glutamate fluxes by introducing them as artificial glutamate scavengers, for instance presented on membrane or artificial lipid complexes, and thus to manipulate brain or neuron function.

The following examples are provided to describe and illustrate the present invention. As such, they should not be construed to limit the scope of the invention. Those in the art will well appreciate that many other embodiments also fall within the scope of the invention, as it is described hereinabove and in the claims.

EXAMPLES

Example 1

Construction of Nucleic Acids and Vectors

A truncated glutamate-aspartate binding protein sequence (SEQ ID NO:4), encoding mature protein without signal peptide, was amplified by PCR using E. coli genomic DNA as a template. The primers used were 5'-ggtaccggaggcgccgcag-gcagcacgctggacaaaatc-3' (SEQ ID NO:5) and 5'-accggtaccg-gcgccgttcagtgccttgtcattcggttc-3' (SEQ ID NO:6). The PCR fragment was cloned into the Kpnl site of FLIPmal-25µ(Fehr et al. 2002) in pRSET vector (Invitrogen), exchanging the maltose binding protein sequence with the YBEJ sequence. The resulting plasmid was named pRSET-FLIP-E-600n.

To improve the pH and chloride tolerance and maturation of the sensor protein, the fragment containing the enhanced YFP (EYFP, CLONTECH) sequence in pRSET-FLIP-E-600n was replaced with the coding sequence of Venus, a variant of YFP with improved pH tolerance and maturation time (Nagai, T., Ibata, K., Park, E. S., Kubota, M., Mikoshiba, K., and Miyawaki, A. (2002) A variant of yellow fluorescent protein with fast and efficient maturation for cell-biological applications. Nat. Biotechnol. 20, 87-90). Affinity mutants carrying substitutions A207G, A207P, A207K, A207M, A207S, A207C, A207R, A207V, A207L, A207Q, A207T, A207F, A207Y, A207N, A207W, A207H, A207D, or S95W were created by site-directed mutagenesis (Kunkel, T. A., Roberts, J. D., and Zakour, R. A. (1987). Rapid and efficient site-specific mutagenesis without phenotypic selection. Methods Enzymol. 154, 367-382).

pRSET-FLIP-E constructs were transferred to E. coli BL21 (DE3)Gold (Stratagene) using electroporation (Sambrook, J., Fritsch, E.F., and Maniatis, T. (1989). Molecular cloning. A laboratory manual. (Cold Spring Harbor NY: Cold Spring Harbor Laboratory Press). FLIP-E proteins expressed in BL21(DE3)Gold strain were extracted and purified as previously described (Fehr et al. 2002). For expression in rat primary neuronal cell culture and PC12 cell culture, FLIP-E 600n and −10µ cassettes were cloned into pDisplay (Invitrogen) as follows: XmaI site and SalI site were introduced on the 5'- and 3'- ends of FLIP-E cassette, respectively, by PCR. The primers used were 5'-gagcccgggatggtgagcaagggcgag-gag-3' (SEQ ID NO:7) and 5'-gaggtcgaccttgtacagctcgtccat-gccgag-3' (SEQ ID NO:8). The PCR fragments were sequenced to confirm that there was no additional PCR error, digested with XmaI/SalI, and cloned into the XmaI/SalI sites of the pDisplay vector. Cell cultures were transfected using a modified calcium phosphate transfection protocol (Xia, Z., Dudek, H., Miranti, C.K., and Greenberg, M.E. (1996). Calcium influx via the NMDA receptor induces immediate early gene transcription by a MAP kinase/ERK-dependent mechanism. J. Neurosci. 16, 5425-5436) or Lipofectamine (Invitrogen).

Example 2

In Vitro Characterization of FLIP-E Nanosensors

A DNA fragment encoding the mature YBEJ protein was fused to ECFP and the Venus sequence at the N- and C-termini, respectively (FIG. 1). Emission spectra and substrate titration curves were obtained by using monochromator microplate reader Safire (Tecan, Austria). Excitation filter was 433±12 nm, emission filters for CFP and YFP emission were 485±12, 528 nm±12 nm, respectively. All analyses were done in 20 mM sodium phosphate buffer, pH 7.0.

Figure 2:
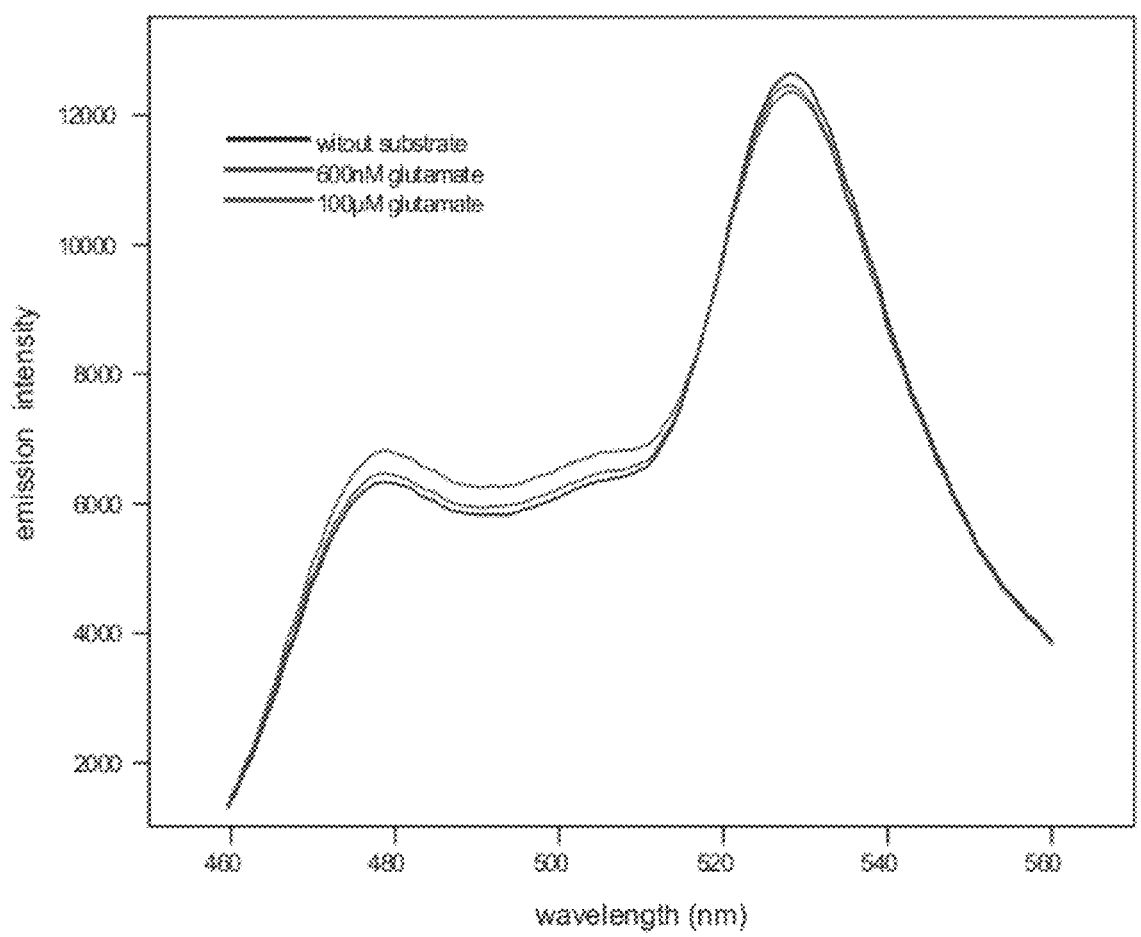
FIG. 2. Spectra of FLIP-E 600n sensor (fluorescent glutamate nanosensor with a $K_d$ for glutamate of 600 nM) at three different concentrations of glutamate: 0 mM (black), at the $K_d$ (blue), and at saturation (red). Curves share an isosbestic point at 520 nm.

Addition of glutamate resulted in an increase in CFP emission and a decrease in YFP emission, suggesting that binding of glutamate to YBEJ results in a conformational change of the chimeric protein potentially due to a relative change in the orientation of the dipoles of the fluorophores (FIG. 2). Since CFP and YFP moieties are assumed to be attached to the same lobe, we speculate that glutamate binding causes the change in dipole-dipole angle of two fluorophores. Interestingly, the ratio and ratio change were in a similar range as compared to other sensors generated so far (Fehr et al., 2002; Fehr et al., 2003; Lager et al., 2003), suggesting that distance changes may not be the primary factor in underlying the mechanisms for FRET changes. Spectra at three different glutamate concentrations (zero, Kd, saturation) reveals an isosbestic point at 520 nm (FIG. 2). The binding constant (Kd) for glutamate was determined to be 600 nM, consistent with data obtained by other methods (de Lorimier et al., 2002). Binding constants for aspartate, glutamine, asparagine were determined to be 1 µM, 100 µM, 300 µM, respectively (see Table 1, below).

In order to expand the range of concentration that can be measured by YBEJ-based glutamate nanosensors, the YBEJ moiety was mutagenized to create nanosensors with lower affinity for glutamate. It has previously been shown that conjugating various fluorophores to sites located at the perimeter of the interdomain cleft that forms the ligand binding site (named "peristeric") changes the ligand-binding affinity in periplasmic binding proteins (de Lorimier et al., 2002). Among the residues tested, mutation of alanine 207 to lysine, methionine, serine, cysteine, arginine, valine, leucine, glutamine, threonine, phenylalanine, tyrosine, aspargine, tryptophan, histidine, aspartate lowered the binding affinity significantly (Table 1). In addition, the mutation of serine 118 to tryptophan, which is suggested to interact with the nitrogen of glutamate, was found to decrease the affinity of the protein. Thus, mutations introduced into the FLIPE nanosensor can yield affinity mutants suitable to cover a wide range of physiological glutamate concentrations.

TABLE 1

| Vector | YbeJ moiety | Kd(M) Glutamate | Kd(M) Aspartate | Kd(M) Glutamine | Kd(M) Asparagine |
|---|---|---|---|---|---|
| FLIPE-600n-1 | WT | $6 \times 10^{-7}$ | $6 \times 10^{-6}$ | $1 \times 10^{-4}$ | $3 \times 10^{-4}$ |
| FLIPE-600n-2 | A207G | $6 \times 10^{-7}$ | $4 \times 10^{-6}$ | $2 \times 10^{-4}$ | n.d. |
| FLIPE-600n-3 | A207P | $6 \times 10^{-7}$ | $4 \times 10^{-6}$ | $2 \times 10^{-4}$ | n.d. |
| FLIPE-3µ | A207K | $3 \times 10^{-6}$ | $2 \times 10^{-5}$ | $7 \times 10^{-4}$ | n.d. |
| FLIPE-5µ | A207M | $5 \times 10^{-6}$ | $3 \times 10^{-5}$ | $1 \times 10^{-3}$ | n.d. |
| FLIPE-5µ-2 | A207S | $5 \times 10^{-6}$ | $3 \times 10^{-5}$ | $1 \times 10^{-3}$ | n.d. |

TABLE 1-continued

| Vector | YbeJ moiety | Kd(M) Glutamate | Kd(M) Aspartate | Kd(M) Glutamine | Kd(M) Asparagine |
|---|---|---|---|---|---|
| FLIPE-6μ | A207C | $6 \times 10^{-6}$ | $5 \times 10^{-5}$ | n.d. | n.d. |
| FLIPE-10μ-1 | A207R | $1 \times 10^{-5}$ | $6 \times 10^{-5}$ | $1 \times 10^{-3}$ | n.d. |
| FLIPE-10μ-2 | A207V | $1 \times 10^{-5}$ | $8 \times 10^{-5}$ | $6 \times 10^{-3}$ | n.d. |
| FLIPE-30μ | A207L | $3 \times 10^{-5}$ | n.d. | n.d. | n.d. |
| FLIPE-40μ-1 | A207Q | $4 \times 10^{-5}$ | $2 \times 10^{-4}$ | $7 \times 10^{-3}$ | n.d. |
| FLIPE-40μ-1 | A207T | $4 \times 10^{-5}$ | $1 \times 10^{-4}$ | $7 \times 10^{-3}$ | n.d. |
| FLIPE-100μ-1 | S95W | $1 \times 10^{-4}$ | n.d. | n.d. | n.d. |
| FLIPE-100μ-2 | A207F | $1 \times 10^{-4}$ | $6 \times 10^{-4}$ | n.d. | n.d. |
| FLIPE-300μ | A207Y | $3 \times 10^{-4}$ | $5 \times 10^{-4}$ | n.d. | n.d. |
| FLIPE-400μ | A207N | $4 \times 10^{-4}$ | $1 \times 10^{-3}$ | n.d. | n.d. |
| FLIPE-1m | A207W | $1 \times 10^{-3}$ | n.d. | n.d. | n.d. |
| FLIPE-2m-1 | A207H | $2 \times 10^{-3}$ | $2 \times 10^{-3}$ | n.d. | n.d. |
| FLIPE-2m-2 | A207D | $2 \times 10^{-3}$ | $9 \times 10^{-4}$ | n.d. | n.d. |

Example 3

In Vivo Characterization of Flip-E

For the in vivo characterization of FLIP-E nanosensors, FLIPE-600n and FLIPE-10μ were cloned into the mammalian expression vector pDisplay (Invitrogen, USA). The pDisplay vector carries a leader sequence which directs the protein to the secretory pathway, and the transmembrane domain which anchors the protein to the plasma membrane, displaying the protein on the extracellular face. Rat hippocampal cells and PC12 cells were transfected with pDisplay FLIPE-600n and -10μ constructs. FRET was imaged 24-48 hours after transfection on a fluorescent microscope (DM IRE2, Leica) with a cooled CoolSnap HQ digital camera (Photometrics). Dual emission intensity ratios were simultaneously recorded following excitation at 436 nm and splitting CFP and Venus emission by DualView with the OI-5-EM filter set (Optical Insights) and Metafluor 6.1r1 software (Universal Imaging).

Figure 3:
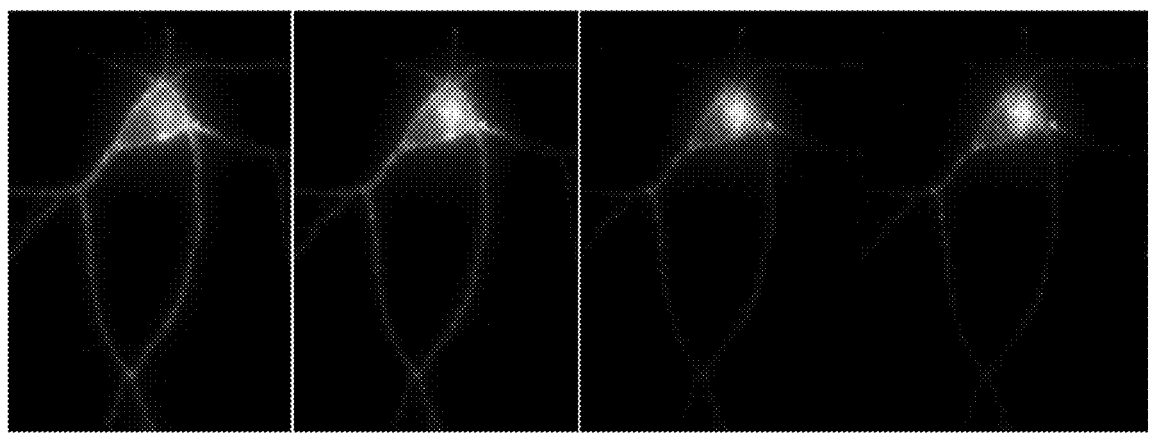
FIG. 3. A hippocampal cell treated with 1 mg/ml trypsin. Images (A-D) were taken at 10 second intervals. Note that signals on the cell surface largely disappear.

The expression of FLIP-E was observed on the plasma membrane of rat hippocampal cell culture, and to some extent also in intracellular compartments, probably in compartments involved in plasma membrane targeting of plasma membrane proteins. When treated with Tyrode's buffer containing 1 mg/mL of trypsin, the majority of fluorescence on the cell surface was eliminated, demonstrating that the FLIPE protein was indeed displayed on the extracellular face of the plasma membrane as expected from the properties of the pDisplay construct (FIG. 3). The nanosensors should thus measure extracellular glutamate levels close to the cell's surface.

Figure 4:
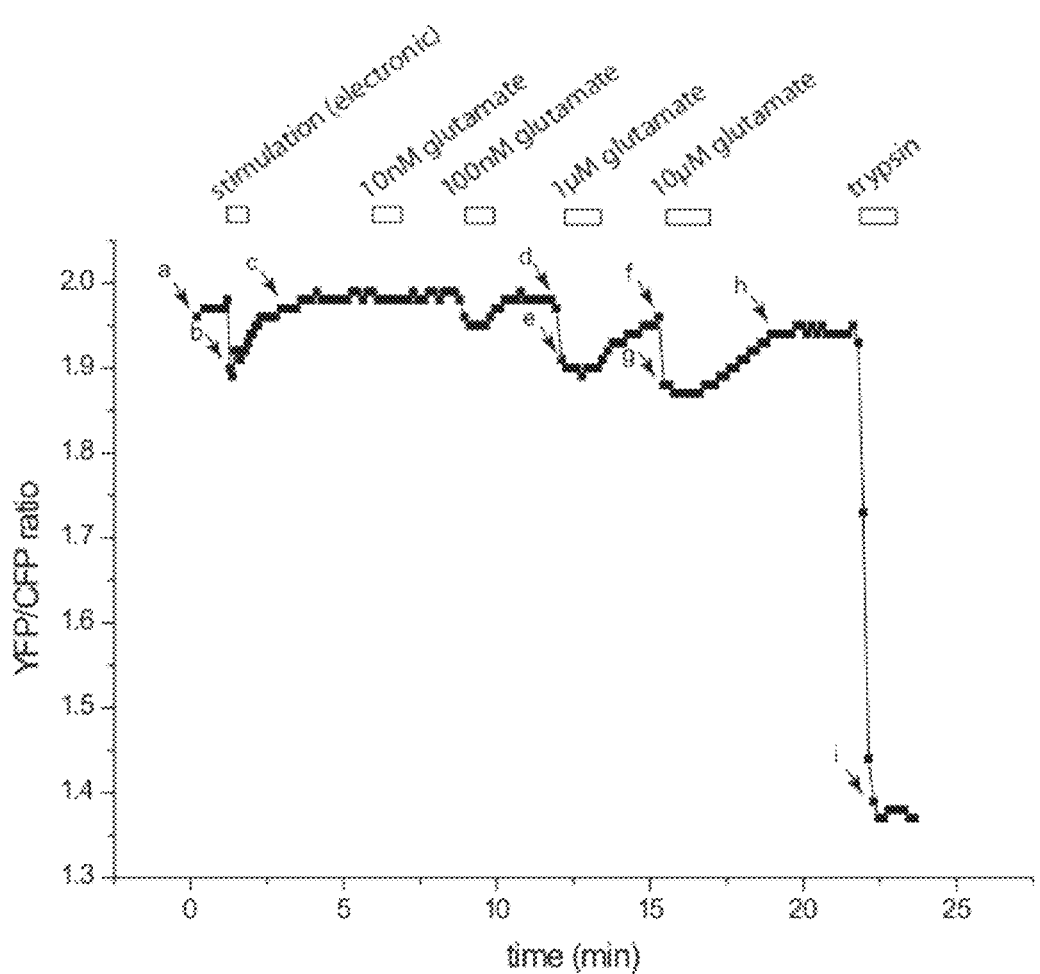
FIG. 4. Emission intensity ratio change in a hippocampal cell expressing FLIP-E 600n sensor. The images are pseudo-colored to indicate the emission intensity ratio change. Open bars above the graph (A) indicate the time point of treatment (stimulation/perfusion with glutamate). Ratio images at the time points indicated by arrows are shown in panel (B), a to i. The change in emission intensity ratio was both observed upon electrical stimulation and upon perfusion with glutamate. The ratio change was not observed when perfusing with low levels of substrate (10 nM glutamate).
Figure 4:
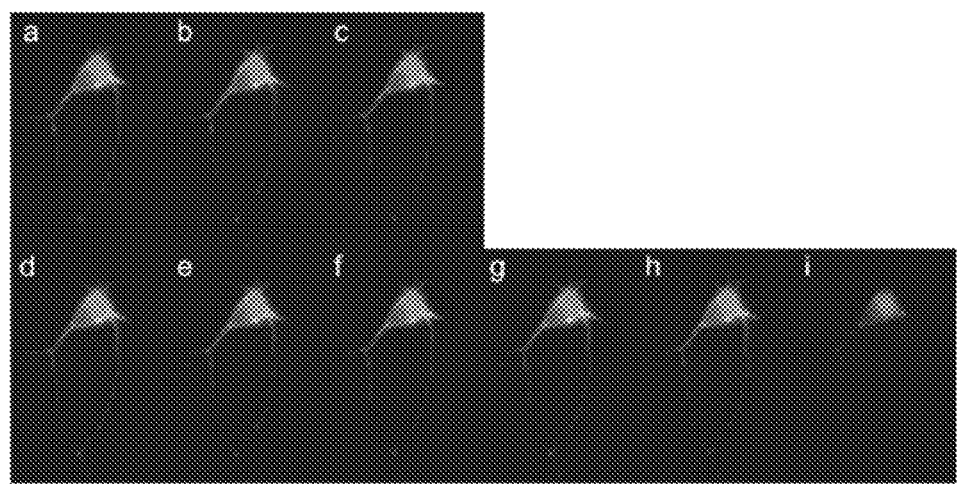

To quantify the intensity of CFP and Venus emission, the fluorescence intensity in the two channels in the periphery of the cell was integrated on a pixel-by-pixel basis, and the CFP/Venus ratio was calculated. When the hippocampal cells displaying FLIPE-600n on the surface were electrically stimulated by passing current pulse, a decrease in CFP/Venus emission ratio was observed (FIG. 4 a-c), suggesting that the glutamate is released from hippocampal cells by membrane depolarization. To confirm that the ratio change is due to changes in the extracellular concentration of glutamate, the cell was perfused with increasing concentrations of glutamate. The emission intensity ratio changed in a concentration dependent manner, (FIG. 4 d-h), indicating that the FLIPE-600n displayed on the cell surface recognizes the extracellular glutamate. The working range of the FLIP-E 600n sensor was between 100 nM to 1 μM, which is consistent with the in vitro working range of FLIPE-600n nanosensor. The CFP/Venus ratio increased when the external medium was washed away by perfusion, suggesting that the change in FRET intensity in vivo is reversible.

Figure 5:
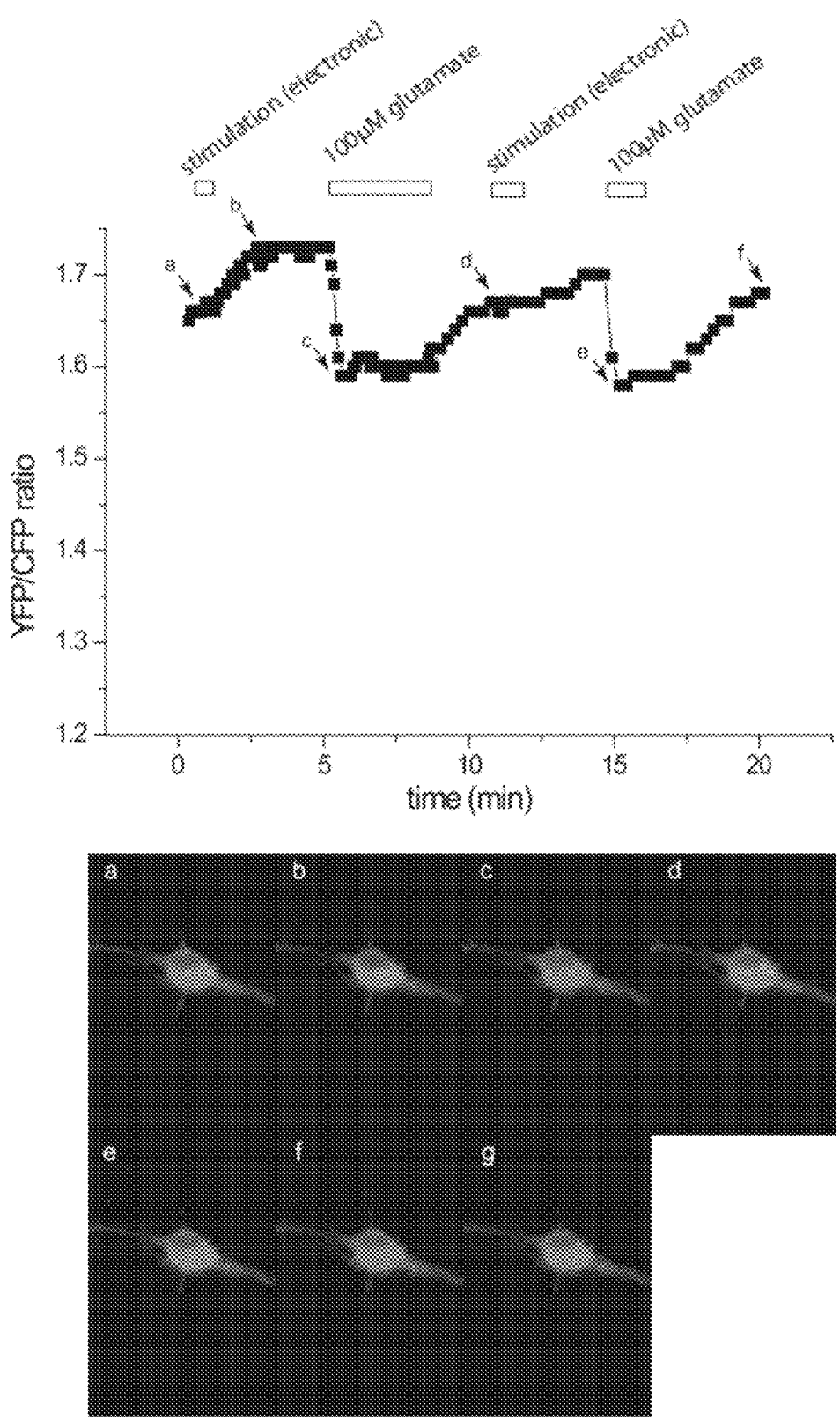
FIG. 5. Emission intensity ratio change in a hippocampal cell expressing FLIP-E 10p sensor (fluorescent glutamate nanosensor with a $K_d$ for glutamate of 10 μM). Open bars above the graph (A) indicate the time point of treatment (stimulation/perfusion with glutamate). Ratio images at the time points indicated by arrow are shown in panel (B), a to g. Electrical stimulation did not cause a large change in the emission intensity ratio, whereas perfusion with 100 µM glutamate induces a reversible ratio change (panel (B), c and e).

In contrast to the cells expressing FLIPE/600n sensor, the CFP/Venus emission intensity change was not observed in cells expressing FLIPE-10μ upon electro-stimulation (FIG. 5). However, a ratio change was observed when the cells were perfused with higher concentrations of glutamate, (FIG. 5 c and e), suggesting that the glutamate concentration change induced by depolarization of the cell was below the working range of FLIP-E 10μ sensor.

The novel nanosensors are thus able to measure glutamate on the surface of neuronal cells and to follow the glutamate secretion of presynaptic neurons directly.

All publications, patents and patent applications discussed herein are incorporated herein by reference. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A fusion protein comprising:
   a glutamate binding protein moiety comprising the amino acid of SEQ ID NO:4;
   a donor fluorescent protein moiety covalently coupled to a first terminus of the glutamate binding protein moiety; and
   an acceptor fluorescent protein moiety covalently coupled to a second terminus of the glutamate binding protein moiety;
   wherein the donor and the acceptor moieties are on the same lobe of the glutamate binding protein moiety, and wherein upon glutamate binding to the glutamate binding protein moiety fluorescence resonance energy transfer (FRET) between the donor fluorescent protein moiety and the acceptor fluorescent protein moiety is altered.

2. The fusion protein of claim 1, wherein said glutamate binding protein moiety consists of the amino acid sequence of SEQ ID NO: 4.

3. The fusion protein of claim 1, wherein said donor fluorescent protein moiety is selected from the group consisting of a GFP, a CFP, a BFP, a YFP and a dsRED.

4. The fusion protein of claim 1, wherein said acceptor fluorescent protein moiety is selected from the group consisting of a GFP, a CFP, a BFP, a YFP and a dsRED.

5. The fusion protein of claim 1, wherein said donor fluorescent protein moiety is CFP and said acceptor fluorescent protein moiety is YFP Venus.

6. The fusion protein of claim 1, further comprising at least one linker moiety.

7. A cell containing the fusion protein of claim 1.

8. The cell of claim 7, wherein the cell is a prokaryote.

9. The cell of claim 7, wherein the cell is *E. coli*.

10. The cell of claim 7, wherein the cell is a eukaryotic cell.

11. The cell of claim 7, wherein the cell is a yeast cell.

12. The cell of claim 7, wherein the cell is an animal cell.

13. The fusion protein of claim 1, further comprising one or more amino acid substitutions that lower the affinity of the glutamate binding protein moiety to glutamate.

14. The fusion protein of claim 13, wherein the altered amino acid is selected from the group consisting of A175G, A175P, A175K, A175M, A175S, A175C, A175R, A175V, A175L, A175Q, A175T, A175F, A175Y, A175N, A175W, A175H, A175D, and S63W of SEQ ID NO:4.

15. A method of detecting changes in the level of extracellular glutamate secreted by a sample of neurons, comprising:
   (a) providing a cell with the fusion protein of claim 1 and the sample of neurons; and
   (b) detecting a change in FRET between said donor fluorescent protein moiety and said acceptor fluorescent protein moiety,
   wherein a change in FRET between said donor moiety and said acceptor moiety indicates a change in the level of extracellular glutamate secreted by the sample of neurons.

16. The method of claim 15, wherein the step of determining FRET comprises measuring light emitted from the acceptor fluorescent protein moiety.

17. The method of claim 15, wherein determining FRET comprises measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety.

18. The method of claim 15, wherein the step of determining FRET comprises measuring the excited state lifetime of the donor moiety.

19. The method of claim 15, wherein said sample of neurons is contained in vivo.

20. The method of claim 15, wherein said sample of neurons is contained in vitro.

21. The method of claim 19, wherein said change in the level of extracellular glutamate is caused by traumatic injury to said neurons.

22. The method of claim 15, wherein said change in the level of extracellular glutamate is associated with a disorder selected from the group consisting of stroke, epilepsy, Huntington disease, AIDS dementia complex, and amyotrophic lateral sclerosis.

23. A method of identifying a compound that modulates neuron excitotoxicity, comprising:
   (a) contacting a cell containing the fusion protein of claim 1 and a sample of neurons with one or more test compounds; and
   (b) determining FRET between said donor fluorescent domain and said acceptor fluorescent domain following said contacting,
   wherein increased or decreased FRET following said contacting the neurons with the one or more test compounds indicates that said one or more test compounds is a compound that modulates neuron excitotoxicity.

24. The method of claim 23, wherein the step of determining FRET comprises measuring light emitted from the acceptor fluorescent protein moiety.

25. The method of claim 23, wherein determining FRET comprises measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety.

26. The method of claim 23, wherein the step of determining FRET comprises measuring the excited state lifetime of the donor moiety.

27. The method of claim 23, wherein said sample of neurons is contained in vivo.

28. The method of claim 23, wherein said sample of neurons is contained in vitro.

* * * * *

SEQUENCE LISTING

```
<160> NUMBER OF SEQ ID NOS: 14

<210> SEQ ID NO 1
<211> LENGTH: 909
<212> TYPE: DNA
<213> ORGANISM: Escherichia coli K12
<220> FEATURE:
<221> NAME/KEY: CDS
<222> LOCATION: (1)..(909)

<400> SEQUENCE: 1 atg caa tta cgt aaa cct gcc aca gca atc ctc gcc ctg gcg ctt tcc      48
Met Gln Leu Arg Lys Pro Ala Thr Ala Ile Leu Ala Leu Ala Leu Ser
1               5                   10                  15 gca gga ctg gca cag gca gat gac gcc gcc ccg gca gcg ggc agt act      96
Ala Gly Leu Ala Gln Ala Asp Asp Ala Ala Pro Ala Ala Gly Ser Thr
```

```
                    20                  25                  30
ctg gac aaa atc gcc aaa aac ggt gtg att gtc gtc ggt cac cgt gaa      144
Leu Asp Lys Ile Ala Lys Asn Gly Val Ile Val Val Gly His Arg Glu
             35                  40                  45 tct tca gtg cct ttc tct tat tac gac aat cag caa aaa gtg gtg ggt      192
Ser Ser Val Pro Phe Ser Tyr Tyr Asp Asn Gln Gln Lys Val Val Gly
 50                  55                  60 tac tcg cag gat tac tcc aac gcc att gtt gaa gca gtg aaa aag aaa      240
Tyr Ser Gln Asp Tyr Ser Asn Ala Ile Val Glu Ala Val Lys Lys Lys
 65                  70                  75                  80 ctc aac aaa ccg gac ttg cag gta aaa ctg att ccg att acc tca caa      288
Leu Asn Lys Pro Asp Leu Gln Val Lys Leu Ile Pro Ile Thr Ser Gln
                 85                  90                  95 aac cgt att cca ctg ctg caa aac ggc act ttc gat ttt gaa tgt ggt      336
Asn Arg Ile Pro Leu Leu Gln Asn Gly Thr Phe Asp Phe Glu Cys Gly
            100                 105                 110 tct acc acc aac aac gtc gaa cgc caa aaa cag gcg gct ttc tct gac      384
Ser Thr Thr Asn Asn Val Glu Arg Gln Lys Gln Ala Ala Phe Ser Asp
            115                 120                 125 act att ttc gtg gtc ggt acg cgc ctg ttg acc aaa aag ggt ggc gat      432
Thr Ile Phe Val Val Gly Thr Arg Leu Leu Thr Lys Lys Gly Gly Asp
        130                 135                 140 atc aaa gat ttt gcc aac ctg aaa gac aaa gcc gta gtc gtc act tcc      480
Ile Lys Asp Phe Ala Asn Leu Lys Asp Lys Ala Val Val Val Thr Ser
145                 150                 155                 160 ggc act acc tct gaa gtt ttg ctc aac aaa ctg aat gaa gag caa aaa      528
Gly Thr Thr Ser Glu Val Leu Leu Asn Lys Leu Asn Glu Glu Gln Lys
                165                 170                 175 atg aat atg cgc atc atc agc gcc aaa gat cac ggt gac tct ttc cgc      576
Met Asn Met Arg Ile Ile Ser Ala Lys Asp His Gly Asp Ser Phe Arg
            180                 185                 190 acc ctg gaa agc ggt cgt gcc gtt gcc ttt atg atg gat gac gct ctg      624
Thr Leu Glu Ser Gly Arg Ala Val Ala Phe Met Met Asp Asp Ala Leu
        195                 200                 205 ctg gcc ggt gaa cgt gcg aaa gcg aag aaa cca gac aac tgg gaa atc      672
Leu Ala Gly Glu Arg Ala Lys Ala Lys Lys Pro Asp Asn Trp Glu Ile
210                 215                 220 gtc ggc aag ccg cag tct cag gag gcc tac ggt tgt atg ttg cgt aaa      720
Val Gly Lys Pro Gln Ser Gln Glu Ala Tyr Gly Cys Met Leu Arg Lys
225                 230                 235                 240 gat gat ccg cag ttc aaa aag ctg atg gat gac acc atc gct cag gtg      768
Asp Asp Pro Gln Phe Lys Lys Leu Met Asp Asp Thr Ile Ala Gln Val
                245                 250                 255 cag acc tcc ggt gaa gcg gaa aaa tgg ttt gat aag tgg ttc aaa aat      816
Gln Thr Ser Gly Glu Ala Glu Lys Trp Phe Asp Lys Trp Phe Lys Asn
            260                 265                 270 cca att ccg ccg aaa aac ctg aac atg aat ttc gaa ctg tca gac gaa      864
Pro Ile Pro Pro Lys Asn Leu Asn Met Asn Phe Glu Leu Ser Asp Glu
        275                 280                 285 atg aaa gca ctg ttc aaa gaa ccg aat gac aag gca ctg aac taa          909
Met Lys Ala Leu Phe Lys Glu Pro Asn Asp Lys Ala Leu Asn
290                 295                 300

<210> SEQ ID NO 2
<211> LENGTH: 302
<212> TYPE: PRT
<213> ORGANISM: Escherichia coli K12

<400> SEQUENCE: 2

Met Gln Leu Arg Lys Pro Ala Thr Ala Ile Leu Ala Leu Ala Leu Ser
 1               5                  10                  15
```

```
Ala Gly Leu Ala Gln Ala Asp Asp Ala Ala Pro Ala Ala Gly Ser Thr
            20                  25                  30

Leu Asp Lys Ile Ala Lys Asn Gly Val Ile Val Val Gly His Arg Glu
            35                  40                  45

Ser Ser Val Pro Phe Ser Tyr Tyr Asp Asn Gln Gln Lys Val Val Gly
    50                  55                  60

Tyr Ser Gln Asp Tyr Ser Asn Ala Ile Val Glu Ala Val Lys Lys Lys
65              70                  75                  80

Leu Asn Lys Pro Asp Leu Gln Val Lys Leu Ile Pro Ile Thr Ser Gln
                85                  90                  95

Asn Arg Ile Pro Leu Leu Gln Asn Gly Thr Phe Asp Phe Glu Cys Gly
                100                 105                 110

Ser Thr Thr Asn Asn Val Glu Arg Gln Lys Gln Ala Ala Phe Ser Asp
            115                 120                 125

Thr Ile Phe Val Val Gly Thr Arg Leu Leu Thr Lys Lys Gly Gly Asp
            130                 135                 140

Ile Lys Asp Phe Ala Asn Leu Lys Asp Lys Ala Val Val Val Thr Ser
145                 150                 155                 160

Gly Thr Thr Ser Glu Val Leu Leu Asn Lys Leu Asn Glu Glu Gln Lys
                165                 170                 175

Met Asn Met Arg Ile Ile Ser Ala Lys Asp His Gly Asp Ser Phe Arg
            180                 185                 190

Thr Leu Glu Ser Gly Arg Ala Val Ala Phe Met Met Asp Asp Ala Leu
            195                 200                 205

Leu Ala Gly Glu Arg Ala Lys Ala Lys Lys Pro Asp Asn Trp Glu Ile
    210                 215                 220

Val Gly Lys Pro Gln Ser Gln Glu Ala Tyr Gly Cys Met Leu Arg Lys
225                 230                 235                 240

Asp Asp Pro Gln Phe Lys Lys Leu Met Asp Asp Thr Ile Ala Gln Val
                245                 250                 255

Gln Thr Ser Gly Glu Ala Glu Lys Trp Phe Asp Lys Trp Phe Lys Asn
            260                 265                 270

Pro Ile Pro Pro Lys Asn Leu Asn Met Asn Phe Glu Leu Ser Asp Glu
            275                 280                 285

Met Lys Ala Leu Phe Lys Glu Pro Asn Asp Lys Ala Leu Asn
    290                 295                 300

<210> SEQ ID NO 3
<211> LENGTH: 810
<212> TYPE: DNA
<213> ORGANISM: Escherichia coli K12
<220> FEATURE:
<221> NAME/KEY: CDS
<222> LOCATION: (1)..(810)

<400> SEQUENCE: 3 ctg gac aaa atc gcc aaa aac ggt gtg att gtc gtc ggt cac cgt gaa      48
Leu Asp Lys Ile Ala Lys Asn Gly Val Ile Val Val Gly His Arg Glu
1               5                   10                  15 tct tca gtg cct ttc tct tat tac gac aat cag caa aaa gtg gtg ggt      96
Ser Ser Val Pro Phe Ser Tyr Tyr Asp Asn Gln Gln Lys Val Val Gly
            20                  25                  30 tac tcg cag gat tac tcc aac gcc att gtt gaa gca gtg aaa aag aaa     144
Tyr Ser Gln Asp Tyr Ser Asn Ala Ile Val Glu Ala Val Lys Lys Lys
        35                  40                  45 ctc aac aaa ccg gac ttg cag gta aaa ctg att ccg att acc tca caa     192
Leu Asn Lys Pro Asp Leu Gln Val Lys Leu Ile Pro Ile Thr Ser Gln
```

```
                50                  55                  60
aac cgt att cca ctg ctg caa aac ggc act ttc gat ttt gaa tgt ggt        240
Asn Arg Ile Pro Leu Leu Gln Asn Gly Thr Phe Asp Phe Glu Cys Gly
 65                  70                  75                  80 tct acc acc aac aac gtc gaa cgc caa aaa cag gcg gct ttc tct gac        288
Ser Thr Thr Asn Asn Val Glu Arg Gln Lys Gln Ala Ala Phe Ser Asp
                 85                  90                  95 act att ttc gtg gtc ggt acg cgc ctg ttg acc aaa aag ggt ggc gat        336
Thr Ile Phe Val Val Gly Thr Arg Leu Leu Thr Lys Lys Gly Gly Asp
            100                 105                 110 atc aaa gat ttt gcc aac ctg aaa gac aaa gcc gta gtc gtc act tcc        384
Ile Lys Asp Phe Ala Asn Leu Lys Asp Lys Ala Val Val Val Thr Ser
        115                 120                 125 ggc act acc tct gaa gtt ttg ctc aac aaa ctg aat gaa gag caa aaa        432
Gly Thr Thr Ser Glu Val Leu Leu Asn Lys Leu Asn Glu Glu Gln Lys
    130                 135                 140 atg aat atg cgc atc atc agc gcc aaa gat cac ggt gac tct ttc cgc        480
Met Asn Met Arg Ile Ile Ser Ala Lys Asp His Gly Asp Ser Phe Arg
145                 150                 155                 160 acc ctg gaa agc ggt cgt gcc gtt gcc ttt atg atg gat gac gct ctg        528
Thr Leu Glu Ser Gly Arg Ala Val Ala Phe Met Met Asp Asp Ala Leu
                165                 170                 175 ctg gcc ggt gaa cgt gcg aaa gcg aag aaa cca gac aac tgg gaa atc        576
Leu Ala Gly Glu Arg Ala Lys Ala Lys Lys Pro Asp Asn Trp Glu Ile
            180                 185                 190 gtc ggc aag ccg cag tct cag gag gcc tac ggt tgt atg ttg cgt aaa        624
Val Gly Lys Pro Gln Ser Gln Glu Ala Tyr Gly Cys Met Leu Arg Lys
        195                 200                 205 gat gat ccg cag ttc aaa aag ctg atg gat gac acc atc gct cag gtg        672
Asp Asp Pro Gln Phe Lys Lys Leu Met Asp Asp Thr Ile Ala Gln Val
    210                 215                 220 cag acc tcc ggt gaa gcg gaa aaa tgg ttt gat aag tgg ttc aaa aat        720
Gln Thr Ser Gly Glu Ala Glu Lys Trp Phe Asp Lys Trp Phe Lys Asn
225                 230                 235                 240 cca att ccg ccg aaa aac ctg aac atg aat ttc gaa ctg tca gac gaa        768
Pro Ile Pro Pro Lys Asn Leu Asn Met Asn Phe Glu Leu Ser Asp Glu
                245                 250                 255 atg aaa gca ctg ttc aaa gaa ccg aat gac aag gca ctg aac                810
Met Lys Ala Leu Phe Lys Glu Pro Asn Asp Lys Ala Leu Asn
            260                 265                 270

<210> SEQ ID NO 4
<211> LENGTH: 270
<212> TYPE: PRT
<213> ORGANISM: Escherichia coli K12

<400> SEQUENCE: 4

Leu Asp Lys Ile Ala Lys Asn Gly Val Ile Val Gly His Arg Glu
 1               5                  10                  15

Ser Ser Val Pro Phe Ser Tyr Tyr Asp Asn Gln Lys Val Val Gly
                20                  25                  30

Tyr Ser Gln Asp Tyr Ser Asn Ala Ile Val Glu Ala Val Lys Lys Lys
            35                  40                  45

Leu Asn Lys Pro Asp Leu Gln Val Lys Leu Ile Pro Ile Thr Ser Gln
        50                  55                  60

Asn Arg Ile Pro Leu Leu Gln Asn Gly Thr Phe Asp Phe Glu Cys Gly
 65                  70                  75                  80

Ser Thr Thr Asn Asn Val Glu Arg Gln Lys Gln Ala Ala Phe Ser Asp
                85                  90                  95
```

```
Thr Ile Phe Val Val Gly Thr Arg Leu Leu Thr Lys Lys Gly Gly Asp
                100                 105                 110
Ile Lys Asp Phe Ala Asn Leu Lys Asp Lys Ala Val Val Thr Ser
            115                 120                 125
Gly Thr Thr Ser Glu Val Leu Leu Asn Lys Leu Asn Glu Glu Gln Lys
130                 135                 140
Met Asn Met Arg Ile Ile Ser Ala Lys Asp His Gly Asp Ser Phe Arg
145                 150                 155                 160
Thr Leu Glu Ser Gly Arg Ala Val Ala Phe Met Met Asp Asp Ala Leu
                165                 170                 175
Leu Ala Gly Glu Arg Ala Lys Ala Lys Lys Pro Asp Asn Trp Glu Ile
            180                 185                 190
Val Gly Lys Pro Gln Ser Gln Glu Ala Tyr Gly Cys Met Leu Arg Lys
        195                 200                 205
Asp Asp Pro Gln Phe Lys Lys Leu Met Asp Asp Thr Ile Ala Gln Val
    210                 215                 220
Gln Thr Ser Gly Glu Ala Glu Lys Trp Phe Asp Lys Trp Phe Lys Asn
225                 230                 235                 240
Pro Ile Pro Pro Lys Asn Leu Asn Met Asn Phe Glu Leu Ser Asp Glu
                245                 250                 255
Met Lys Ala Leu Phe Lys Glu Pro Asn Asp Lys Ala Leu Asn
                260                 265                 270

<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5
ggtaccggag gcgccgcagg cagcacgctg gacaaaatc                          39

<210> SEQ ID NO 6
<211> LENGTH: 39
<212> TYPE: DNA
<213> ORGANISM: Artificial Sequence
<220> FEATURE:
<223> OTHER INFORMATION: Primer

<400> SEQUENCE: 6
accggtaccg gcgccgttca gtgccttgtc attcggttc                          39

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gagcccggga tggtgagcaa gggcgaggag                                    30

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
gaggtcgacc ttgtacagct cgtccatgcc gag                                33
```

<210> SEQ ID NO 9
<211> LENGTH: 5206
<212> TYPE: DNA
<213> ORGANISM: Artificial Sequence
<220> FEATURE:
<223> OTHER INFORMATION: DNA sequence of pRSETB FLIP-E 600n vector

<400> SEQUENCE: 9

| | | | | | |
|---|---|---|---|---|---|
| atctcgatcc | cgcgaaatta | atacgactca | ctatagggag | accacaacgg | tttccctcta | 60 |
| gataattttg | tttaacttta | agaaggagat | atacatatgc | ggggttctca | tcatcatcat | 120 |
| catcatggta | tggctagcat | gactggtgga | cagcaaatgg | gtcgggatct | gtacgacgat | 180 |
| gacgataagg | atccgggccg | catggtgagc | aagggcgagg | agctgttcac | cggggtggtg | 240 |
| cccatcctgg | tcgagctgga | cggcgacgta | aacggccaca | agttcagcgt | gtccggcgag | 300 |
| ggcgagggcg | atgccaccta | cggcaagctg | accctgaagt | tcatctgcac | caccggcaag | 360 |
| ctgcccgtgc | cctggcccac | cctcgtgacc | accctgacct | ggggcgtgca | gtgcttcagc | 420 |
| cgctaccccg | accacatgaa | gcagcacgac | ttcttcaagt | ccgccatgcc | cgaaggctac | 480 |
| gtccaggagc | gcaccatctt | cttcaaggac | gacggcaact | acaagacccg | cgccgaggtg | 540 |
| aagttcgagg | gcgacaccct | ggtgaaccgc | atcgagctga | agggcatcga | cttcaaggag | 600 |
| gacggcaaca | tcctggggca | caagctggag | tacaactaca | tcagccacaa | cgtctatatc | 660 |
| accgccgaca | agcagaagaa | cggcatcaag | gccaacttca | agatccgcca | caacatcgag | 720 |
| gacggcagcg | tgcagctcgc | cgaccactac | cagcagaaca | cccccatcgg | cgacggcccc | 780 |
| gtgctgctgc | ccgacaacca | ctacctgagc | acccagtccg | ccctgagcaa | agaccccaac | 840 |
| gagaagcgcg | atcacatggt | cctgctggag | ttcgtgaccg | ccgccgggat | cactctcggc | 900 |
| atggacgagc | tgtacaaggg | tggtaccgga | ggcgccgcag | gcagcacgct | ggacaaaatc | 960 |
| gccaaaaacg | gtgtgattgt | cgtcggtcac | cgtgaatctt | cagtgccttt | ctcttattac | 1020 |
| gacaatcagc | aaaaagtggt | gggttactcg | caggattact | ccaacgccat | tgttgaagca | 1080 |
| gtgaaaagaa | aactcaacaa | accggacttg | caggtaaaac | tgattccgat | tacctcacaa | 1140 |
| aaccgtattc | cactgctgca | aaacggcact | ttcgattttg | aatgtggttc | taccaccaac | 1200 |
| aacgtcgaac | gccaaaaaca | ggcggctttc | tctgacacta | ttttcgtggt | cggtacgcgc | 1260 |
| ctgttgacca | aaaagggtgg | cgatatcaaa | gattttgcca | acctgaaaga | caaagccgta | 1320 |
| gtcgtcactt | ccggcactac | ctctgaagtt | ttgctcaaca | actgaatga | agagcaaaaa | 1380 |
| atgaatatgc | gcatcatcag | cgccaaagat | cacggtgact | ctttccgcac | cctggaaagc | 1440 |
| ggtcgtgccg | ttgcctttat | gatggatgac | gctctgctgg | ccggtgaacg | tgcgaaagcg | 1500 |
| aagaaaccag | acaactggga | aatcgtcggc | aagccgcagt | ctcaggaggc | ctacggttgt | 1560 |
| atgttgcgta | agatgatcc | gcagttcaaa | aagctgatgg | atgacaccat | cgctcaggtg | 1620 |
| cagacctccg | gtgaagcgga | aaatggtttt | gataagtggt | tcaaaaatcc | aattccgccg | 1680 |
| aaaaacctga | acatgaattt | cgaactgtca | gacgaaatga | agcactgtt | caaagaaccg | 1740 |
| aatgacaagg | cactgaacgg | cgccggtacc | ggtggaatgt | tgagcaaggg | cgaggagctg | 1800 |
| ttcaccgggg | tggtgcccat | cctggtcgag | ctggacggcg | acgtaaacgg | ccacaagttc | 1860 |
| agcgtgtccg | gcgagggcga | gggcgatgcc | acctacggca | agctgaccct | gaagttcatc | 1920 |
| tgcaccaccg | gcaagctgcc | cgtgccctgg | cccaccctcg | tgaccacctt | cggctacggc | 1980 |
| ctgcagtgct | tcgcccgcta | ccccgaccac | atgaagcagc | acgacttctt | caagtccgcc | 2040 |
| atgcccgaag | gctacgtcca | ggagcgcacc | atcttcttca | aggacgacgg | caactacaag | 2100 |

```
acccgcgccg aggtgaagtt cgagggcgac accctggtga accgcatcga gctgaagggc    2160
atcgacttca aggaggacgg caacatcctg gggcacaagc tggagtacaa ctacaacagc    2220
cacaacgtct atatcatggc cgacaagcag aagaacggca tcaaggtgaa cttcaagatc    2280
cgccacaaca tcgaggacgg cagcgtgcag ctcgccgacc actaccagca gaacaccccc    2340
atcggcgacg cccccgtgct gctgcccgac aaccactacc tgagctacca gtccgccctg    2400
agcaaagacc ccaacgagaa gcgcgatcac atggtcctgc tggagttcgt gaccgccgcc    2460
gggatcactc tcggcatgga cgagctgtac aagtaaaagc ttgatccggc tgctaacaaa    2520
gcccgaaagg aagctgagtt ggctgctgcc accgctgagc aataactagc ataacccctt    2580
ggggcctcta acgggtctt gaggggtttt ttgctgaaag gaggaactat atccggatct    2640
ggcgtaatag cgaagaggcc cgcaccgatc gcccttccca acagttgcgc agcctgaatg    2700
gcgaatggga cgcgccctgt agcggcgcat taagcgcggc gggtgtggtg gttacgcgca    2760
gcgtgaccgc tacacttgcc agcgccctag cgcccgctcc tttcgctttc ttcccttcct    2820
ttctcgccac gttcgccggc tttccccgtc aagctctaaa tcggggctc cctttagggt    2880 tccgatttag agctttacgg cacctcgacc gcaaaaaact tgatttgggt gatggttcac    2940
gtagtgggcc atcgccctga tagacggttt ttcgcccttt gacgttggag tccacgttct    3000
ttaatagtgg actcttgttc caaactggaa caacactcaa ccctatcgcg gtctattctt    3060
ttgatttata agggattttg ccgatttcgg cctattggtt aaaaaatgag ctgatttaac    3120
aaatatttaa cgcgaatttt aacaaaatat taacgtttac aatttcgcct gatgcggtat    3180
tttctcctta cgcatctgtg cggtatttca caccgcatac aggtggcact tttcggggaa    3240
atgtgcgcgg aacccctatt tgtttatttt tctaaataca ttcaaatatg tatccgctca    3300
tgagacaata accctgataa atgcttcaat aatattgaaa aaggaagagt atgagtattc    3360
aacatttccg tgtcgccctt attcccttt tgcggcatt ttgccttcct gttttgctc    3420 acccagaaac gctggtgaaa gtaaaagatg ctgaagatca gttgggtgca cgagtgggtt    3480
acatcgaact ggatctcaac agcggtaaga tccttgagag ttttcgcccc gaagaacgtt    3540
ttccaatgat gagcactttt aaagttctgc tatgtgatac actattatcc cgtattgacg    3600
ccgggcaaga gcaactcggt cgccgcatac actattctca gaatgacttg gttgagtact    3660
caccagtcac agaaaagcat cttacggatg gcatgacagt aagagaatta tgcagtgctg    3720
ccataaccat gagtgataac actgcggcca acttacttct gacaacgatc ggaggaccga    3780
aggagctaac cgcttttttg cacaacatgg gggatcatgt aactcgcctt gatcgttggg    3840
aaccggagct gaatgaagcc ataccaaacg acgagagtga ccacgatg cctgtagcaa    3900 tgccaacaac gttgcgcaaa ctattaactg gcgaactact tactctagct tcccggcaac    3960
aattaataga ctgaatggag gcggataaag ttgcaggacc acttctgcgc tcggcccttc    4020
cggctggctg gtttattgct gataaatctg gagccggtga gcgtgggtct cgcggtatca    4080
ttgcagcact ggggccagat ggtaagcgct cccgtatcgt agttatctac acgacgggga    4140
gtcaggcaac tatggatgaa cgaaatagac agatcgctga taggtgcc tcactgatta    4200 agcattggta actgtcagac caagtttact catatatact ttagattgat ttaaaacttc    4260 attttttaatt taaaaggatc taggtgaaga tccttttgat aatctcatg accaaaatcc    4320 cttaacgtga gttttcgttc cactgagcgt cagaccccgt agaaaagatc aaaggatctt    4380
cttgagatcc ttttttttctg cgcgtaatct gctgcttgca acaaaaaaa ccaccgctac    4440 cagcggtggt ttgtttgccg gatcaagagc taccaactct ttttccgaag gtaactggct    4500
```

-continued

| | |
|---|---|
| tcagcagagc gcagatacca aatactgtcc ttctagtgta gccgtagtta ggccaccact | 4560 |
| tcaagaactc tgtagcaccg cctacatacc tcgctctgct aatcctgtta ccagtggctg | 4620 |
| ctgccagtgg cgataagtcg tgtcttaccg ggttggactc aagacgatag ttaccggata | 4680 |
| aggcgcagcg gtcgggctga acgggggggtt cgtgcacaca gcccagcttg gagcgaacga | 4740 |
| cctacaccga actgagatac ctacagcgtg agctatgaga agcgccacg cttcccgaag | 4800 |
| ggagaaaggc ggacaggtat ccggtaagcg gcagggtcgg aacaggagag cgcacgaggg | 4860 |
| agcttccagg gggaaacgcc tggtatcttt atagtcctgt cgggtttcgc cacctctgac | 4920 |
| ttgagcgtcg atttttgtga tgctcgtcag ggggcggag cctatggaaa aacgccagca | 4980 |
| acgcggcctt tttacggttc ctgggcttttt gctggccttt tgctcacatg ttctttcctg | 5040 |
| cgttatcccc tgattctgtg gataaccgta ttaccgcctt tgagtgagct gataccgctc | 5100 |
| gccgcagccg aacgaccgag cgcagcgagt cagtgagcga ggaagcggaa gagcgcccaa | 5160 |
| tacgcaaacc gcctctcccc gcgcgttggc cgattcatta atgcag | 5206 |

<210> SEQ ID NO 10
<211> LENGTH: 5206
<212> TYPE: DNA
<213> ORGANISM: Artificial Sequence
<220> FEATURE:
<223> OTHER INFORMATION: DNA sequence of pRSETB FLIP-E 10micron vector

<400> SEQUENCE: 10

| | |
|---|---|
| atctcgatcc cgcgaaatta atacgactca ctatagggag accacaacgg tttccctcta | 60 |
| gataattttg tttaacttta agaaggagat atacatatgc ggggttctca tcatcatcat | 120 |
| catcatggta tggctagcat gactggtgga cagcaaatgg gtcgggatct gtacgacgat | 180 |
| gacgataagg atccgggccg catggtgagc aagggcgagg agctgttcac cggggtggtg | 240 |
| cccatcctgg tcgagctgga cggcgacgta aacggccaca agttcagcgt gtccggcgag | 300 |
| ggcgagggcg atgccaccta cggcaagctg accctgaagt tcatctgcac caccggcaag | 360 |
| ctgcccgtgc cctggcccac cctcgtgacc accctgacct ggggcgtgca gtgcttcagc | 420 |
| cgctacccccg accacatgaa gcagcacgac ttcttcaagt ccgccatgcc cgaaggctac | 480 |
| gtccaggagc gcaccatctt cttcaaggac gacggcaact acaagacccg cgccgaggtg | 540 |
| aagttcgagg gcgacaccct ggtgaaccgc atcgagctga agggcatcga cttcaaggag | 600 |
| gacggcaaca tcctggggca caagctggag tacaactaca tcagccacaa cgtctatatc | 660 |
| accgccgaca agcagaagaa cggcatcaag gccaacttca agatccgcca caacatcgag | 720 |
| gacggcagcg tgcagctcgc cgaccactac cagcagaaca ccccccatcgg cgacggcccc | 780 |
| gtgctgctgc ccgacaacca ctacctgagc acccagtccg ccctgagcaa agaccccaac | 840 |
| gagaagcgcg atcacatggt cctgctggag ttcgtgaccg ccgccgggat cactctcggc | 900 |
| atggacgagc tgtacaaggg tggtaccgga ggcgccgcag gcagcacgct ggacaaaatc | 960 |
| gccaaaaacg gtgtgattgt cgtcggtcac cgtgaatctt cagtgccttt ctcttattac | 1020 |
| gacaatcagc aaaaagtggt gggttactcg caggattact ccaacgccat tgttgaagca | 1080 |
| gtgaaaaaga aactcaacaa accggacttg caggtaaaac tgattccgat tacctcacaa | 1140 |
| aaccgtattc cactgctgca aaacggcact ttcgattttg aatgtggttc taccaccaac | 1200 |
| aacgtcgaac gccaaaaaca ggcggctttc tctgacacta ttttcgtggt cggtacgcgc | 1260 |
| ctgttgacca aaaaggggtgg cgatatcaaa gattttgcca acctgaaaga caagccgta | 1320 |
| gtcgtcactt ccggcactac ctctgaagtt ttgctcaaca aactgaatga agagcaaaaa | 1380 |

```
atgaatatgc gcatcatcag cgccaaagat cacggtgact ctttccgcac cctggaaagc   1440
ggtcgtgccg ttgcctttat gatggatgac cggctgctgg ccggtgaacg tgcgaaagcg   1500
aagaaaccag acaactggga atcgtcggc aagccgcagt ctcaggaggc ctacggttgt    1560
atgttgcgta agatgatcc gcagttcaaa aagctgatgg atgacaccat cgctcaggtg    1620
cagacctccg gtgaagcgga aaatggtttt gataagtggt tcaaaaatcc aattccgccg   1680
aaaaacctga acatgaattt cgaactgtca gacgaaatga agcactgtt caaagaaccg    1740 aatgacaagg cactgaacgg cgccggtacc ggtggaatgg tgagcaaggg cgaggagctg   1800
ttcaccgggg tggtgcccat cctggtcgag ctggacggcg acgtaaacgg ccacaagttc   1860
agcgtgtccg gcgagggcga gggcgatgcc acctacggca agctgaccct gaagttcatc   1920
tgcaccaccg gcaagctgcc cgtgccctgg cccaccctcg tgaccacctt cggctacggc   1980
ctgcagtgct tcgcccgcta ccccgaccac atgaagcagc acgacttctt caagtccgcc   2040
atgcccgaag ctacgtcca ggagcgcacc atcttcttca aggacgacgg caactacaag   2100
acccgcgccg aggtgaagtt cgagggcgac accctggtga accgcatcga gctgaagggc   2160
atcgacttca aggaggacgg caacatcctg gggcacaagc tggagtacaa ctacaacagc   2220
cacaacgtct atatcatggc cgacaagcag aagaacggca tcaaggtgaa cttcaagatc   2280
cgccacaaca tcgaggacgg cagcgtgcag ctcgccgacc actaccagca gaacacccc   2340 atcggcgacg gccccgtgct gctgcccgac aaccactacc tgagctacca gtccgccctg   2400
agcaaagacc ccaacgagaa gcgcgatcac atggtcctgc tggagttcgt gaccgccgcc   2460
gggatcactc tcggcatgga cgagctgtac aagtaaaagc ttgatccggc tgctaacaaa   2520
gcccgaaagg aagctgagtt ggctgctgcc accgctgagc aataactagc ataaccctt    2580 ggggcctcta acgggtctt gaggggtttt tgctgaaag gaggaactat atccggatct     2640
ggcgtaatag cgaagaggcc cgcaccgatc gcccttccca cagttgcgc agcctgaatg    2700 gcgaatggga cgcgccctgt agcggcgcat taagcgcggc gggtgtggtg ttacgcgca    2760 gcgtgaccgc tacacttgcc agcgccctag cgcccgctcc tttcgctttc ttcccttcct   2820
ttctcgccac gttcgccggc tttccccgtc aagctctaaa tcggggctc cctttagggt    2880 tccgatttag agctttacgg cacctcgacc gcaaaaaact tgatttgggt gatggttcac   2940
gtagtgggcc atcgccctga tagacggttt ttcgcccttt gacgttggag tccacgttct   3000
ttaatagtgg actcttgttc caaactggaa caacactcaa ccctatcgcg gtctattctt   3060
ttgatttata agggattttg ccgatttcgg cctattggtt aaaaaatgag ctgatttaac   3120
aaatatttaa cgcgaatttt aacaaaatat taacgtttac aatttcgcct gatgcggtat   3180
tttctcctta cgcatctgtg cggtatttca caccgcatac aggtggcact tttcggggaa   3240
atgtgcgcgg aacccctatt tgtttatttt tctaaataca ttcaaatatg tatccgctca   3300
tgagacaata accctgataa atgcttcaat aatattgaaa aaggaagagt atgagtattc   3360
aacatttccg tgtcgccctt attcctttt ttgcggcatt ttgccttcct gtttttgctc    3420
acccagaaac gctggtgaaa gtaaaagatg ctgaagatca gttgggtgca cgagtgggtt   3480
acatcgaact ggatctcaac agcggtaaga tccttgagag ttttcgcccc gaagaacgtt   3540
ttccaatgat gagcactttt aaagttctgc tatgtgtatac actattatcc cgtattgacg   3600
ccgggcaaga gcaactcggt cgccgcatac actattctca gaatgacttg gttgagtact   3660
caccagtcac agaaaagcat cttacggatg gcatgacagt aagagaatta tgcagtgctg   3720
ccataaccat gagtgataac actgcggcca acttacttct gacaacgatc ggaggaccga   3780
```

```
aggagctaac cgcttttttg cacaacatgg gggatcatgt aactcgcctt gatcgttggg    3840
aaccggagct gaatgaagcc ataccaaacg acgagagtga caccacgatg cctgtagcaa    3900
tgccaacaac gttgcgcaaa ctattaactg gcgaactact tactctagct tcccggcaac    3960
aattaataga ctgaatggag gcggataaag ttgcaggacc acttctgcgc tcggcccttc    4020
cggctggctg gtttattgct gataaatctg gagccggtga gcgtgggtct cgcggtatca    4080
ttgcagcact ggggccagat ggtaagcgct cccgtatcgt agttatctac acgacgggga    4140
gtcaggcaac tatggatgaa cgaaatagac agatcgctga gataggtgcc tcactgatta    4200
agcattggta actgtcagac caagtttact catatatact ttagattgat ttaaaacttc    4260
atttttaatt taaaaggatc taggtgaaga tcctttttga taatctcatg accaaaatcc    4320
cttaacgtga gttttcgttc cactgagcgt cagaccccgt agaaaagatc aaaggatctt    4380
cttgagatcc ttttttttctg cgcgtaatct gctgcttgca acaaaaaaa ccaccgctac    4440 cagcggtggt ttgtttgccg gatcaagagc taccaactct ttttccgaag gtaactggct    4500
tcagcagagc gcagatacca atactgtcc ttctagtgta gccgtagtta ggccaccact    4560
tcaagaactc tgtagcaccg cctacatacc tcgctctgct aatcctgtta ccagtggctg    4620
ctgccagtgg cgataagtcg tgtcttaccg ggttggactc aagacgatag ttaccggata    4680
aggcgcagcg gtcgggctga acggggggtt cgtgcacaca gcccagcttg gagcgaacga    4740
cctacaccga actgagatac ctacagcgtg agctatgaga aagcgccacg cttcccgaag    4800
ggagaaaggc ggacaggtat ccggtaagcg gcagggtcgg aacaggagag cgcacgaggg    4860
agcttccagg gggaaacgcc tggtatcttt atagtcctgt cgggtttcgc cacctctgac    4920
ttgagcgtcg atttttgtga tgctcgtcag ggggggcggag cctatggaaa aacgccagca    4980
acgcggcctt tttacggttc ctgggctttt gctggccttt tgctcacatg ttctttcctg    5040
cgttatcccc tgattctgtg gataaccgta ttaccgcctt tgagtgagct gataccgctc    5100
gccgcagccg aacgaccgag cgcagcgagt cagtgagcga ggaagcggaa gagcgcccaa    5160
tacgcaaacc gcctctcccc gcgcgttggc cgattcatta atgcag              5206
```

<210> SEQ ID NO 11
<211> LENGTH: 7603
<212> TYPE: DNA
<213> ORGANISM: Artificial Sequence
<220> FEATURE:
<223> OTHER INFORMATION: DNA sequence of pDisplay FLIP-E 600n

<400> SEQUENCE: 11

```
gcgcgcgttg acattgatta ttgactagtt attaatagta atcaattacg gggtcattag     60
ttcatagccc atatatggag ttccgcgtta cataacttac ggtaaatggc ccgcctggct    120
gaccgcccaa cgaccccccgc ccattgacgt caataatgac gtatgttccc atagtaacgc    180
caatagggac tttccattga cgtcaatggg tggactattt acggtaaact gcccacttgg    240
cagtacatca agtgtatcat atgccaagta cgccccctat tgacgtcaat gacggtaaat    300
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta taagcaga gctctctggc    600 taactagaga acccactgct tactggctta tcgaaattaa tacgactcac tatagggaga    660
```

```
cccaagcttg gtaccgagct cggatccact agtaacggcc gccagtgtgc tggaattcgg      720
cttggggata tccaccatgg agacagacac actcctgcta tgggtactgc tgctctgggt      780
tccaggttcc actggtgact atccatatga tgttccagat tatgctgggg cccagccggc      840
cagatctccc gggatggtga gcaagggcga ggagctgttc accggggtgg tgcccatcct      900
ggtcgagctg gacggcgacg taaacggcca caagttcagc gtgtccggcg agggcgaggg      960
cgatgccacc tacggcaagc tgaccctgaa gttcatctgc accaccggca agctgcccgt     1020
gcccctggcc cccctcgtga ccaccctgac ctggggcgtg cagtgcttca gccgctaccc     1080
cgaccacatg aagcagcacg acttcttcaa gtccgccatg cccgaaggct acgtccagga     1140
gcgcaccatc ttcttcaagg acgacggcaa ctacaagacc cgcgccgagg tgaagttcga     1200
gggcgacacc ctggtgaacc gcatcgagct gaagggcatc gacttcaagg aggacggcaa     1260
catcctgggg cacaagctgg agtacaacta catcagccac aacgtctata tcaccgccga     1320
caagcagaag aacggcatca aggccaactt caagatccgc cacaacatcg aggacggcag     1380
cgtgcagctc gccgaccact accagcagaa cacccccatc ggcgacggcc ccgtgctgct     1440
gcccgacaac cactacctga gcacccagtc cgccctgagc aaagacccca cgagaagcg      1500 cgatcacatg gtcctgctgg agttcgtgac cgccgccggg atcactctcg gcatggacga     1560
gctgtacaag ggtggtaccg gaggcgccgc aggcagcacg ctggacaaaa tcgccaaaaa     1620
cggtgtgatt gtcgtcggtc accgtgaatc ttcagtgcct ttctcttatt acgacaatca     1680
gcaaaaagtg gtgggttact cgcaggatta ctccaacgcc attgttgaag cagtgaaaaa     1740
gaaactcaac aaaccggact tgcaggtaaa actgattccg attacctcac aaaaccgtat     1800
tccactgctg caaaacggca ctttcgattt tgaatgtggt tctaccacca caacgtcga      1860 acgccaaaaa caggcggctt tctctgacac tattttcgtg gtcggtacgc gcctgttgac     1920
caaaaagggt ggcgatatca agatttttgc caacctgaaa gacaaagccg tagtcgtcac     1980
ttccggcact acctctgaag ttttgctcaa caaactgaat gaagagcaaa aatgaatat      2040 gcgcatcatc agcgccaaag atcacggtga ctcttttccgc accctggaaa gcggtcgtgc     2100
cgttgccttt atgatggatg acgctctgct ggccggtgaa cgtgcgaaag cgaagaaacc     2160
agacaactgg gaaatcgtcg gcaagccgca gtctcaggag gcctacggtt gtatgttgcg     2220
taaagatgat ccgcagttca aaaagctgat ggatgacacc atcgctcagg tgcagacctc     2280
cggtgaagcg gaaaaatggt ttgataagtg gttcaaaaat ccaattccgc cgaaaaacct     2340
gaacatgaat ttcgaactgt cagacgaaat gaaagcactg ttcaaagaac cgaatgacaa     2400
ggcactgaac ggcgccggta ccggtggaat ggtgagcaag ggcgaggagc tgttcaccgg     2460
ggtggtgccc atcctggtcg agctggacgg cgacgtaaac ggccacaagt tcagcgtgtc     2520
cggcgagggc gagggcgatg ccacctacgg caagctgacc ctgaagttca tctgcaccac     2580
cggcaagctg cccgtgccct ggcccaccct cgtgaccacc ttcggctacg gcctgcagtg     2640
cttcgcccgc taccccgacc acatgaagca gcacgacttc ttcaagtccg ccatgcccga     2700
aggctacgtc caggagcgca ccatcttctt caaggacgac ggcaactaca agacccgcgc     2760
cgaggtgaag ttcgagggcg acaccctggt gaaccgcatc gagctgaagg gcatcgactt     2820
caaggaggac ggcaacatcc tggggcacaa gctggagtac aactacaaca gccacaacgt     2880
ctatatcatg gccgacaagc agaagaacgg catcaaggtg aacttcaaga tccgccacaa     2940
catcgaggac ggcagcgtgc agctcgccga ccactaccag cagaacaccc ccatcggcga     3000
cggccccgtg ctgctgcccg acaaccacta cctgagctac cagtccgccc tgagcaaaga     3060
```

```
ccccaacgag aagcgcgatc acatggtcct gctggagttc gtgaccgccg ccgggatcac    3120
tctcggcatg gacgagctgt acaaggtcga cgaacaaaaa ctcatctcag aagaggatct    3180
gaatgctgtg ggccaggaca cgcaggaggt catcgtggtg ccacactcct tgcccttaa    3240 ggtggtggtg atctcagcca tcctggccct ggtggtgctc accatcatct cccttatcat    3300
cctcatcatg ctttggcaga gaagccacg ttaggcggcc gctcgagatc agcctcgact    3360
gtgccttcta gttgccagcc atctgttgtt tgcccctccc ccgtgccttc cttgaccctg    3420
gaaggtgcca ctcccactgt cctttcctaa taaaatgagg aaattgcatc gcattgtctg    3480
agtaggtgtc attctattct ggggggtggg gtggggcagg acagcaaggg ggaggattgg    3540
gaagacaata gcaggcatgc tggggatgcg gtgggctcta tggcttctga ggcggaaaga    3600
accagtggcg gtaatacggt tatccacaga atcaggggat aacgcaggaa agaacatgtg    3660
agcaaaaggc cagcaaaagg ccaggaaccg taaaaaggcc gcgttgctgg cgttttccca    3720
taggctccgc ccccctgacg agcatcacaa aaatcgacgc tcaagtcaga ggtggcgaaa    3780
cccgacagga ctataaagat accaggcgtt tccccctgga agctccctcg tgcgctctcc    3840
tgttccgacc ctgccgctta ccggatacct gtccgccttt ctcccttcgg aagcgtggc    3900 gctttctcat agctcacgct gtaggtatct cagttcggtg taggtcgttc gctccaagct    3960
gggctgtgtg cacgaaccc cgttcagcc gaccgctgc gccttatccg gtaactatcg    4020
tcttgagtcc aacccggtaa gacacgactt atcgccactg gcagcagcca ctggtaacag    4080
gattagcaga gcgaggtatg taggcggtgc tacagagttc ttgaagtggt ggcctaacta    4140
cggctacact agaaggacag tatttggtat ctgcgctctg ctgaagccag ttaccttcgg    4200
aaaaagagtt ggtagctctt gatccggcaa acaaaccacc gctggtagcg gtggtttttt    4260
tgtttgcaag cagcagatta cgcgcagaaa aaaggatct caagaagatc ctttgatctt    4320
ttctacgggg tctgacgctc agtggaacga aaactcacgt taagggattt tggtcatgag    4380
attatcaaaa aggatcttca cctagatcct tttaaattaa aaatgaagtt ttaaatcaat    4440
ctaaagtata tatgagtaac ctgaggctat ggcaggcct gccgcccga cgttggctgc    4500 gagccctggg ccttcacccg aacttggggg gtggggtggg gaaaaggaag aaacgcgggc    4560
gtattggccc caatgggtc tcggtggggt atcgacagag tgccagccct gggaccgaac    4620
cccgcgttta tgaacaaacg acccaacacc gtgcgtttta ttctgtcttt ttattgccgt    4680
catagcgcgg gttccttccg gtattgtctc cttccgtgtt tcagttagcc tcccctagg    4740 gtgggcgaag aactccagca tgagatcccc gcgctggagg atcatccagc cggcgtcccg    4800
gaaaacgatt ccgaagccca acctttcata aaggcggcg gtggaatcga aatctcgtga    4860
tggcaggttg ggcgtcgctt ggtcggtcat ttcgaaccc agagtcccgc tcagaagaac    4920
tcgtcaagaa ggcgatagaa ggcgatgcgc tgcgaatcgg gagcggcgat accgtaaagc    4980
acgaggaagc ggtcagccca ttcgccgcca agctcttcag caatatcacg ggtagccaac    5040
gctatgtcct gatagcggtc cgccacaccc agccggccac agtcgatgaa tccagaaaag    5100
cggccatttt ccaccatgat attcggcaag caggcatcgc catgggtcac gacgagatcc    5160
tcgccgtcgg gcatgctcgc cttgagcctg gcgaacagtt cggctggcgc gagccctga    5220 tgctcttgat catcctgatc gacaagaccg gcttccatcc gagtacgtgc tcgctcgatg    5280
cgatgtttcg cttggtggtc gaatgggcag gtagccggat caagcgtatg cagccgccgc    5340
attgcatcag ccatgatgga tactttctcg gcaggagcaa ggtgagatga caggagatcc    5400
tgccccggca cttcgcccaa tagcagccag tcccttcccg cttcagtgac aacgtcgagc    5460
```

```
acagctgcgc aaggaacgcc cgtcgtggcc agccacgata gccgcgctgc ctcgtcttgc    5520
agttcattca gggcaccgga caggtcggtc ttgacaaaaa gaaccgggcg ccctgcgct    5580 gacagccgga acacgcggc atcagagcag ccgattgtct gttgtgccca gtcatagccg    5640
aatagcctct ccacccaagc ggccggagaa cctgcgtgca atccatcttg ttcaatcatg    5700
cgaaacgatc ctcatcctgt ctcttgatcg atctttgcaa aagcctaggc ctccaaaaaa    5760
gcctcctcac tacttctgga atagctcaga ggccgaggag gcggcctcgg cctctgcata    5820
aataaaaaaa attagtcagc catggggcgg agaatgggcg gaactgggcg gagttagggg    5880
cgggatgggc ggagttaggg gcgggactat ggttgctgac taattgagat gcatgctttg    5940
catacttctg cctgctgggg agcctgggga cttttccacac ctggttgctg actaattgag    6000
atgcatgctt tgcatacttc tgcctgctgg ggagcctggg gactttccac accctaactg    6060
acacacattc cacagctggt tctttccgcc tcaggactct ccttttttca ataaatcaat    6120
ctaaagtata tatgagtaaa cttggtctga cagttaccaa tgcttaatca gtgaggcacc    6180
tatctcagcg atctgtctat ttcgttcatc catagttgcc tgactccccg tcgtgtagat    6240
aactacgata cgggagggct taccatctgg ccccagtgct gcaatgatac cgcgagaccc    6300
acgctcaccg gctccagatt tatcagcaat aaaccagcca gccggaaggg ccgagcgcag    6360
aagtggtcct gcaactttat ccgcctccat ccagtctatt aattgttgcc gggaagctag    6420
agtaagtagt tcgccagtta atagtttgcg caacgttgtt gccattgcta caggcatcgt    6480
ggtgtcacgc tcgtcgtttg gtatggcttc attcagctcc ggttcccaac gatcaaggcg    6540
agttacatga tcccccatgt tgtgcaaaaa agcggttagc tccttcggtc ctccgatcgt    6600
tgtcagaagt aagttggccg cagtgttatc actcatggtt atggcagcac tgcataattc    6660
tcttactgtc atgccatccg taagatgctt ttctgtgact ggtgagtact caaccaagtc    6720
attctgagaa tagtgtatgc ggcgaccgag ttgctcttgc ccggcgtcaa tacgggataa    6780
taccgcgcca catagcagaa ctttaaaagt gctcatcatt ggaaaacgtt cttcggggcg    6840
aaaactctca aggatcttac cgctgttgag atccagttcg atgtaaccca ctcgtgcacc    6900
caactgatct tcagcatctt ttactttcac cagcgtttct gggtgagcaa aaacaggaag    6960
gcaaaatgcc gcaaaaaagg gaataagggc gacacggaaa tgttgaatac tcatactctt    7020
cctttttcaa tattattgaa gcatttatca gggttattgt ctcatgagcg gatacatatt    7080
tgaatgtatt tagaaaaata aacaaatagg ggttccgcgc acatttcccc gaaaagtgcc    7140
acctgacgcg cccctgtagcg gcgcattaag cgcggcgggt gtggtggtta cgcgcagcgt    7200
gaccgctaca cttgccagcg ccctagcgcc cgctcctttc gctttcttcc cttcctttct    7260
cgccacgttc gccggctttc cccgtcaagc tctaaatcgg gggctccctt tagggttccg    7320
atttagtgct ttacggcacc tcgaccccaa aaaacttgat tagggtgatg gttcacgtag    7380
tgggccatcg ccctgataga cggttttttcg ccctttgacg ttggagtcca cgttctttaa    7440
tagtggactc ttgttccaaa ctggaacaac actcaaccct atctcggtct attcttttga    7500
tttataaggg attttgccga tttcggccta ttggttaaaa aatgagctga tttaacaaaa    7560
atttaacgcg aattttaaca aaatattaac gcttacaatt tac                     7603
```

<210> SEQ ID NO 12
<211> LENGTH: 7603
<212> TYPE: DNA
<213> ORGANISM: Artificial Sequence
<220> FEATURE:
<223> OTHER INFORMATION: DNA sequence of pDisplay FLIP-E 10micron

<400> SEQUENCE: 12

```
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgaccccgc ccattgacgt caataatgac gtatgttccc atagtaacgc     180
caatagggac tttccattga cgtcaatggg tggactattt acggtaaact gcccacttgg     240
cagtacatca agtgtatcat atgccaagta cgccccctat tgacgtcaat gacggtaaat     300
ggcccgcctg gcattatgcc cagtacatga ccttatggga cttcctact tggcagtaca      360
tctacgtatt agtcatcgct attaccatgg tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta tataagcaga gctctctggc     600
taactagaga acccactgct tactggctta tcgaaattaa tacgactcac tatagggaga     660
cccaagcttg gtaccgagct cggatccact agtaacggcc gccagtgtgc tggaattcgg     720
cttggggata tccaccatgg agacagacac actcctgcta tgggtactgc tgctctgggt     780
tccaggttcc actggtgact atccatatga tgttccagat tatgctgggg cccagccggc     840
cagatctccc gggatggtga gcaagggcga ggagctgttc accggggtgg tgcccatcct     900
ggtcgagctg gacggcgacg taaacggcca agttcagc gtgtccggcg agggcgaggg     960
cgatgccacc tacggcaagc tgaccctgaa gttcatctgc accaccggca agctgcccgt    1020
gccctggccc accctcgtga ccaccctgac ctggggcgtg cagtgcttca gccgctaccc    1080
cgaccacatg aagcagcacg acttcttcaa gtccgccatg cccgaaggct acgtccagga    1140
gcgcaccatc ttcttcaagg acgacggcaa ctacaagacc cgcgccgagg tgaagttcga    1200
gggcgacacc ctggtgaacc gcatcgagct gaagggcatc gacttcaagg aggacggcaa    1260
catcctgggg cacaagctgg agtacaacta catcagccac aacgtctata tcaccgccga    1320
caagcagaag aacggcatca aggccaactt caagatccgc cacaacatcg aggacggcag    1380
cgtgcagctc gccgaccact accagcagaa cacccccatc ggcgacggcc ccgtgctgct    1440
gcccgacaac cactacctga gcacccagtc cgccctgagc aaagacccca acgagaagcg    1500
cgatcacatg gtcctgctgg agttcgtgac cgccgccggg atcactctcg gcatggacga    1560
gctgtacaag ggtggtaccg gaggcgccgc aggcagcacg ctggacaaaa tcgccaaaaa    1620
cggtgtgatt gtcgtcggtc accgtgaatc ttcagtgcct ttctcttatt acgacaatca    1680
gcaaaaagtg gtgggttact cgcaggatta ctccaacgcc attgttgaag cagtgaaaaa    1740
gaaactcaac aaaccggact tgcaggtaaa actgattccg attacctcac aaaaccgtat    1800
tccactgctg caaaacggca ctttcgattt tgaatgtggt tctaccacca acaacgtcga    1860
acgccaaaaa caggcggctt tctctgacac tattttcgtg gtcggtacgc gcctgttgac    1920
caaaaagggt ggcgatatca aagattttgc caacctgaaa gacaaagccg tagtcgtcac    1980
ttccggcact acctctgaag ttttgctcaa caaactgaat gaagagcaaa aaatgaatat    2040
gcgcatcatc agcgccaaag atcacggtga ctctttccgc accctggaaa gcggtcgtgc    2100
cgttgccttt atgatggatg accggctgct ggccggtgaa cgtgcgaaag cgaagaaacc    2160
agacaactgg gaaatcgtcg gcaagccgca gtctcaggag gcctacggtt gtatgttgcg    2220
taaagatgat ccgcagttca aaaagctgat ggatgacacc atcgctcagg tgcagacctc    2280
cggtgaagcg gaaaaatggt ttgataagtg gttcaaaaat ccaattccgc cgaaaaacct    2340
```

```
gaacatgaat tcgaactgt cagacgaaat gaaagcactg ttcaaagaac cgaatgacaa   2400
ggcactgaac ggcgccggta ccggtggaat ggtgagcaag ggcgaggagc tgttcaccgg   2460
ggtggtgccc atcctggtcg agctggacgg cgacgtaaac ggccacaagt tcagcgtgtc   2520
cggcgagggc gagggcgatg ccacctacgg caagctgacc ctgaagttca tctgcaccac   2580
cggcaagctg cccgtgccct ggcccaccct cgtgaccacc ttcggctacg gcctgcagtg   2640
cttcgcccgc taccccgacc acatgaagca gcacgacttc ttcaagtccg ccatgcccga   2700
aggctacgtc caggagcgca ccatcttctt caaggacgac ggcaactaca agacccgcgc   2760
cgaggtgaag ttcgagggcg acaccctggt gaaccgcatc gagctgaagg gcatcgactt   2820
caaggaggac ggcaacatcc tggggcacaa gctggagtac aactacaaca gccacaacgt   2880
ctatatcatg gccgacaagc agaagaacgg catcaaggtg aacttcaaga tccgccacaa   2940
catcgaggac ggcagcgtgc agctcgccga ccactaccag cagaacaccc ccatcggcga   3000
cggccccgtg ctgctgcccg acaaccacta cctgagctac cagtccgccc tgagcaaaga   3060
ccccaacgag aagcgcgatc acatggtcct gctggagttc gtgaccgccg ccgggatcac   3120
tctcggcatg gacgagctgt acaaggtcga cgaacaaaaa ctcatctcag aagaggatct   3180
gaatgctgtg ggccaggaca cgcaggaggt catcgtggtg ccacactcct tgccctttaa   3240
ggtggtggtg atctcagcca tcctggccct ggtggtgctc accatcatct cccttatcat   3300
cctcatcatg ctttggcaga agaagccacg ttaggcggcc gctcgagatc agcctcgact   3360
gtgccttcta gttgccagcc atctgttgtt tgccccctcc ccgtgccttc cttgaccctg   3420
gaaggtgcca ctcccactgt cctttcctaa taaaatgagg aaattgcatc gcattgtctg   3480
agtaggtgtc attctattct ggggggtggg gtggggcagg acagcaaggg ggaggattgg   3540
gaagacaata gcaggcatgc tggggatgcg gtgggctcta tggcttctga ggcggaaaga   3600
accagtggcg gtaatacggt tatccacaga atcaggggat aacgcaggaa agaacatgtg   3660
agcaaaaggc cagcaaaagg ccaggaaccg taaaaaggcc gcgttgctgg cgttttttcca   3720 taggctccgc ccccctgacg agcatcacaa aaatcgacgc tcaagtcaga ggtggcgaaa   3780
cccgacagga ctataaagat accaggcgtt tcccccctgga agctccctcg tgcgctctcc   3840
tgttccgacc ctgccgctta ccggatacct gtccgccttt ctcccttcgg aagcgtggc   3900 gctttctcat agctcacgct gtaggtatct cagttcggtg taggtcgttc gctccaagct   3960
gggctgtgtg cacgaacccc ccgttcagcc cgaccgctgc gccttatccg gtaactatcg   4020
tcttgagtcc aacccggtaa gacacgactt atcgccactg gcagcagcca ctggtaacag   4080
gattagcaga gcgaggtatg taggcggtgc tacagagttc ttgaagtggt ggcctaacta   4140
cggctacact agaaggacag tatttggtat ctgcgctctg ctgaagccag ttaccttcgg   4200
aaaaagagtt ggtagctctt gatccggcaa acaaaccacc gctggtagcg gtggtttttt   4260
tgtttgcaag cagcagatta cgcgcagaaa aaaaggatct caagaagatc ctttgatctt   4320
ttctacgggg tctgacgctc agtggaacga aaactcacgt taagggattt tggtcatgag   4380
attatcaaaa aggatcttca cctagatcct tttaaattaa aatgaagtt ttaaatcaat   4440 ctaaagtata tatgagtaac ctgaggctat ggcagggcct gccgccccga cgttggctgc   4500
gagccctggg ccttcacccg aacttggggg gtggggtggg gaaaaggaag aaacgcgggc   4560
gtattggccc caatggggtc tcggtggggt atcgacagag tgccagccct gggaccgaac   4620
cccgcgttta tgaacaaacg acccaacacc gtgcgtttta ttctgtcttt ttattgccgt   4680
catagcgcgg gttccttccg gtattgtctc cttccgtgtt tcagttagcc tcccccctagg   4740
```

```
gtgggcgaag aactccagca tgagatcccc gcgctggagg atcatccagc cggcgtcccg    4800
gaaaacgatt ccgaagccca acctttcata gaaggcggcg gtggaatcga aatctcgtga    4860
tggcaggttg ggcgtcgctt ggtcggtcat ttcgaacccc agagtcccgc tcagaagaac    4920
tcgtcaagaa ggcgatagaa ggcgatgcgc tgcgaatcgg gagcggcgat accgtaaagc    4980
acgaggaagc ggtcagccca ttcgccgcca agctcttcag caatatcacg ggtagccaac    5040
gctatgtcct gatagcggtc cgccacaccc agccggccac agtcgatgaa tccagaaaag    5100
cggccatttt ccaccatgat attcggcaag caggcatcgc catgggtcac gacgagatcc    5160
tcgccgtcgg gcatgctcgc cttgagcctg gcgaacagtt cggctggcgc gagccsctga    5220
tgctcttgat catcctgatc gacaagaccg gcttccatcc gagtacgtgc tcgctcgatg    5280
cgatgtttcg cttggtggtc gaatgggcag gtagccggat caagcgtatg cagccgccgc    5340
attgcatcag ccatgatgga tactttctcg gcaggagcaa ggtgagatga caggagatcc    5400
tgccccggca cttcgcccaa tagcagccag tcccttcccg cttcagtgac aacgtcgagc    5460
acagctgcgc aaggaacgcc cgtcgtggcc agccacgata ccgcgctgc ctcgtcttgc     5520 agttcattca gggcaccgga caggtcggtc ttgacaaaaa gaaccgggcg ccctgcgct     5580 gacagccgga acacggcggc atcagagcag ccgattgtct gttgtgccca gtcatagccg    5640
aatagcctct ccacccaagc ggccggagaa cctgcgtgca atccatcttg ttcaatcatg    5700
cgaaacgatc ctcatcctgt ctcttgatcg atctttgcaa aagcctaggc ctccaaaaaa    5760
gcctcctcac tacttctgga atagctcaga ggccgaggag gcggcctcgg cctctgcata    5820
aataaaaaaa attagtcagc catggggcgg agaatgggcg gaactgggcg gagttagggg    5880
cgggatgggc ggagttaggg gcgggactat ggttgctgac taattgagat gcatgctttg    5940
catacttctg cctgctgggg agcctgggga cttccacac ctggttgctg actaattgag     6000
atgcatgctt tgcatacttc tgcctgctgg ggagcctggg gacttccac accctaactg     6060 acacacattc cacagctggt tctttccgcc tcaggactct ccttttttca ataaatcaat    6120
ctaaagtata tatgagtaaa cttggtctga cagttaccaa tgcttaatca gtgaggcacc    6180
tatctcagcg atctgtctat ttcgttcatc catagttgcc tgactccccg tcgtgtagat    6240
aactacgata cgggagggct taccatctgg ccccagtgct gcaatgatac cgcgagaccc    6300
acgctcaccg gctccagatt tatcagcaat aaaccagcca gccggaaggg ccgagcgcag    6360
aagtggtcct gcaactttat ccgcctccat ccagtctatt aattgttgcc gggaagctag    6420
agtaagtagt tcgccagtta atagtttgcg caacgttgtt gccattgcta caggcatcgt    6480
ggtgtcacgc tcgtcgtttg gtatggcttc attcagctcc ggttcccaac gatcaaggcg    6540
agttacatga tcccccatgt tgtgcaaaaa agcggttagc tccttcggtc ctccgatcgt    6600
tgtcagaagt aagttggccg cagtgttatc actcatggtt atggcagcac tgcataattc    6660
tcttactgtc atgccatccg taagatgctt ttctgtgact ggtgagtact caaccaagtc    6720
attctgagaa tagtgtatgc ggcgaccgag ttgctcttgc ccggcgtcaa tacgggataa    6780
taccgcgcca catagcagaa ctttaaaagt gctcatcatt ggaaaacgtt cttcggggcg    6840
aaaactctca aggatcttac cgctgttgag atccagttcg atgtaaccca ctcgtgcacc    6900
caactgatct tcagcatctt ttactttcac cagcgtttct gggtgagcaa aaacaggaag    6960
gcaaaatgcc gcaaaaaagg gaataagggc gacacggaaa tgttgaatac tcatactctt    7020 ccttttttcaa tattattgaa gcatttatca gggttattgt ctcatgagcg gatacatatt    7080
tgaatgtatt tagaaaaata aacaaatagg ggttccgcgc acatttcccc gaaaagtgcc    7140
```

-continued

```
acctgacgcg ccctgtagcg gcgcattaag cgcggcgggt gtggtggtta cgcgcagcgt    7200
gaccgctaca cttgccagcg ccctagcgcc cgctcctttc gctttcttcc cttcctttct    7260
cgccacgttc gccggctttc cccgtcaagc tctaaatcgg gggctccctt tagggttccg    7320
atttagtgct ttacggcacc tcgaccccaa aaaacttgat tagggtgatg gttcacgtag    7380
tgggccatcg ccctgataga cggttttttcg ccctttgacg ttggagtcca cgttctttaa    7440
tagtggactc ttgttccaaa ctggaacaac actcaaccct atctcggtct attcttttga    7500
tttataaggg atttttgccga tttcggccta ttggttaaaa aatgagctga tttaacaaaa    7560
atttaacgcg aattttaaca aaatattaac gcttacaatt tac                      7603
```

<210> SEQ ID NO 13
<211> LENGTH: 799
<212> TYPE: PRT
<213> ORGANISM: Artificial Sequence
<220> FEATURE:
<223> OTHER INFORMATION: Amino acid sequence of FLIP-E 600n (expressed as 6xHis fusion in pRSET FLIP-E 600n)

<400> SEQUENCE: 13

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Met Val Ser Lys Gly Glu Glu Leu Phe Thr Gly Val Val
        35                  40                  45

Pro Ile Leu Val Glu Leu Asp Gly Asp Val Asn Gly His Lys Phe Ser
    50                  55                  60

Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Trp Gly Val Gln Cys Phe Ser Arg Tyr Pro Asp
            100                 105                 110

His Met Lys Gln His Asp Phe Phe Lys Ser Ala Met Pro Glu Gly Tyr
        115                 120                 125

Val Gln Glu Arg Thr Ile Phe Phe Lys Asp Asp Gly Asn Tyr Lys Thr
    130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Ile Ser His Asn Val Tyr Ile Thr Ala Asp Lys
            180                 185                 190

Gln Lys Asn Gly Ile Lys Ala Asn Phe Lys Ile Arg His Asn Ile Glu
        195                 200                 205

Asp Gly Ser Val Gln Leu Ala Asp His Tyr Gln Gln Asn Thr Pro Ile
    210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
            260                 265                 270

Tyr Lys Gly Gly Thr Gly Gly Ala Ala Gly Ser Thr Leu Asp Lys Ile
```

```
                275                 280                 285
Ala Lys Asn Gly Val Ile Val Gly His Arg Glu Ser Ser Val Pro
290                 295                 300
Phe Ser Tyr Tyr Asp Asn Gln Gln Lys Val Val Gly Tyr Ser Gln Asp
305                 310                 315                 320
Tyr Ser Asn Ala Ile Val Glu Ala Val Lys Lys Leu Asn Lys Pro
            325                 330                 335
Asp Leu Gln Val Lys Leu Ile Pro Ile Thr Ser Gln Asn Arg Ile Pro
                340                 345                 350
Leu Leu Gln Asn Gly Thr Phe Asp Phe Glu Cys Gly Ser Thr Thr Asn
            355                 360                 365
Asn Val Glu Arg Gln Lys Gln Ala Ala Phe Ser Asp Thr Ile Phe Val
        370                 375                 380
Val Gly Thr Arg Leu Leu Thr Lys Lys Gly Asp Ile Lys Asp Phe
385                 390                 395                 400
Ala Asn Leu Lys Asp Lys Ala Val Val Thr Ser Gly Thr Thr Ser
                405                 410                 415
Glu Val Leu Leu Asn Lys Leu Asn Glu Glu Gln Lys Met Asn Met Arg
                420                 425                 430
Ile Ile Ser Ala Lys Asp His Gly Asp Ser Phe Arg Thr Leu Glu Ser
        435                 440                 445
Gly Arg Ala Val Ala Phe Met Met Asp Asp Ala Leu Leu Ala Gly Glu
    450                 455                 460
Arg Ala Lys Ala Lys Lys Pro Asp Asn Trp Glu Ile Val Gly Lys Pro
465                 470                 475                 480
Gln Ser Gln Glu Ala Tyr Gly Cys Met Leu Arg Lys Asp Asp Pro Gln
                485                 490                 495
Phe Lys Lys Leu Met Asp Asp Thr Ile Ala Gln Val Gln Thr Ser Gly
                500                 505                 510
Glu Ala Glu Lys Trp Phe Asp Lys Trp Phe Lys Asn Pro Ile Pro Pro
        515                 520                 525
Lys Asn Leu Asn Met Asn Phe Glu Leu Ser Asp Glu Met Lys Ala Leu
530                 535                 540
Phe Lys Glu Pro Asn Asp Lys Ala Leu Asn Gly Ala Gly Thr Gly Gly
545                 550                 555                 560
Met Val Ser Lys Gly Glu Glu Leu Phe Thr Gly Val Val Pro Ile Leu
                565                 570                 575
Val Glu Leu Asp Gly Asp Val Asn Gly His Lys Phe Ser Val Ser Gly
            580                 585                 590
Glu Gly Glu Gly Asp Ala Thr Tyr Gly Lys Leu Thr Leu Lys Phe Ile
        595                 600                 605
Cys Thr Thr Gly Lys Leu Pro Val Pro Trp Pro Thr Leu Val Thr Thr
    610                 615                 620
Phe Gly Tyr Gly Leu Gln Cys Phe Ala Arg Tyr Pro Asp His Met Lys
625                 630                 635                 640
Gln His Asp Phe Phe Lys Ser Ala Met Pro Glu Gly Tyr Val Gln Glu
                645                 650                 655
Arg Thr Ile Phe Phe Lys Asp Asp Gly Asn Tyr Lys Thr Arg Ala Glu
            660                 665                 670
Val Lys Phe Glu Gly Asp Thr Leu Val Asn Arg Ile Glu Leu Lys Gly
        675                 680                 685
Ile Asp Phe Lys Glu Asp Gly Asn Ile Leu Gly His Lys Leu Glu Tyr
    690                 695                 700
```

```
Asn Tyr Asn Ser His Asn Val Tyr Ile Met Ala Asp Lys Gln Lys Asn
705                 710                 715                 720

Gly Ile Lys Val Asn Phe Lys Ile Arg His Asn Ile Glu Asp Gly Ser
            725                 730                 735

Val Gln Leu Ala Asp His Tyr Gln Gln Asn Thr Pro Ile Gly Asp Gly
        740                 745                 750

Pro Val Leu Leu Pro Asp Asn His Tyr Leu Ser Tyr Gln Ser Ala Leu
    755                 760                 765

Ser Lys Asp Pro Asn Glu Lys Arg Asp His Met Val Leu Leu Glu Phe
770                 775                 780

Val Thr Ala Ala Gly Ile Thr Leu Gly Met Asp Glu Leu Tyr Lys
785                 790                 795

<210> SEQ ID NO 14
<211> LENGTH: 764
<212> TYPE: PRT
<213> ORGANISM: Artificial Sequence
<220> FEATURE:
<223> OTHER INFORMATION: Amino acid sequence of FLIP-E 10micron
      (expressed as 6xHis fusion in pRSET FLIP-E 10micron)

<400> SEQUENCE: 14

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Gly Thr Gly Gly Ala Ala Gly Ser Thr Leu Asp Lys Ile Ala Lys Asn
                245                 250                 255

Gly Val Ile Val Val Gly His Arg Glu Ser Ser Val Pro Phe Ser Tyr
            260                 265                 270
```

```
Tyr Asp Asn Gln Gln Lys Val Gly Tyr Ser Gln Asp Tyr Ser Asn
        275                 280                 285
Ala Ile Val Glu Ala Val Lys Lys Leu Asn Lys Pro Asp Leu Gln
290                 295                 300
Val Lys Leu Ile Pro Ile Thr Ser Gln Asn Arg Ile Pro Leu Leu Gln
305                 310                 315                 320
Asn Gly Thr Phe Asp Phe Glu Cys Gly Ser Thr Thr Asn Asn Val Glu
                325                 330                 335
Arg Gln Lys Gln Ala Ala Phe Ser Asp Thr Ile Phe Val Val Gly Thr
                340                 345                 350
Arg Leu Leu Thr Lys Lys Gly Gly Asp Ile Lys Asp Phe Ala Asn Leu
                355                 360                 365
Lys Asp Lys Ala Val Val Thr Ser Gly Thr Thr Ser Glu Val Leu
370                 375                 380
Leu Asn Lys Leu Asn Glu Glu Gln Lys Met Asn Met Arg Ile Ile Ser
385                 390                 395                 400
Ala Lys Asp His Gly Asp Ser Phe Arg Thr Leu Glu Ser Gly Arg Ala
                405                 410                 415
Val Ala Phe Met Met Asp Asp Arg Leu Leu Ala Gly Glu Arg Ala Lys
                420                 425                 430
Ala Lys Lys Pro Asp Asn Trp Glu Ile Val Gly Lys Pro Gln Ser Gln
                435                 440                 445
Glu Ala Tyr Gly Cys Met Leu Arg Lys Asp Asp Pro Gln Phe Lys Lys
450                 455                 460
Leu Met Asp Asp Thr Ile Ala Gln Val Gln Thr Ser Gly Glu Ala Glu
465                 470                 475                 480
Lys Trp Phe Asp Lys Trp Phe Lys Asn Pro Ile Pro Pro Lys Asn Leu
                485                 490                 495
Asn Met Asn Phe Glu Leu Ser Asp Glu Met Lys Ala Leu Phe Lys Glu
                500                 505                 510
Pro Asn Asp Lys Ala Leu Asn Gly Ala Gly Thr Gly Gly Met Val Ser
                515                 520                 525
Lys Gly Glu Glu Leu Phe Thr Gly Val Val Pro Ile Leu Val Glu Leu
530                 535                 540
Asp Gly Asp Val Asn Gly His Lys Phe Ser Val Ser Gly Glu Gly Glu
545                 550                 555                 560
Gly Asp Ala Thr Tyr Gly Lys Leu Thr Leu Lys Phe Ile Cys Thr Thr
                565                 570                 575
Gly Lys Leu Pro Val Pro Trp Pro Thr Leu Val Thr Thr Phe Gly Tyr
                580                 585                 590
Gly Leu Gln Cys Phe Ala Arg Tyr Pro Asp His Met Lys Gln His Asp
                595                 600                 605
Phe Phe Lys Ser Ala Met Pro Glu Gly Tyr Val Gln Glu Arg Thr Ile
610                 615                 620
Phe Phe Lys Asp Asp Gly Asn Tyr Lys Thr Arg Ala Glu Val Lys Phe
625                 630                 635                 640
Glu Gly Asp Thr Leu Val Asn Arg Ile Glu Leu Lys Gly Ile Asp Phe
                645                 650                 655
Lys Glu Asp Gly Asn Ile Leu Gly His Lys Leu Glu Tyr Asn Tyr Asn
                660                 665                 670
Ser His Asn Val Tyr Ile Met Ala Asp Lys Gln Lys Asn Gly Ile Lys
                675                 680                 685
Val Asn Phe Lys Ile Arg His Asn Ile Glu Asp Gly Ser Val Gln Leu
690                 695                 700
```

```
Ala Asp His Tyr Gln Gln Asn Thr Pro Ile Gly Asp Gly Pro Val Leu
705                 710                 715                 720

Leu Pro Asp Asn His Tyr Leu Ser Tyr Gln Ser Ala Leu Ser Lys Asp
            725                 730                 735

Pro Asn Glu Lys Arg Asp His Met Val Leu Leu Glu Phe Val Thr Ala
            740                 745                 750

Ala Gly Ile Thr Leu Gly Met Asp Glu Leu Tyr Lys
            755                 760
```